United States Patent
Klofta et al.

(10) Patent No.: US 11,534,373 B2
(45) Date of Patent: Dec. 27, 2022

(54) WET WIPES COMPRISING A FIBROUS STRUCTURE AND A LIQUID COMPOSITION

(71) Applicant: The Procter & Gamble Company, Cincinnati, OH (US)

(72) Inventors: Thomas James Klofta, Cincinnati, OH (US); Steven Lee Barnholtz, West Chester, OH (US); Christopher Scott Cameron, Cincinnati, OH (US); Mario Castillo, Cincinnati, OH (US); Randall Glenn Marsh, Hamilton, OH (US); Pamela Marie Morison, Cincinnati, OH (US); Wendy Qin, Mason, OH (US); Jeffrey David Turner, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1265 days.

(21) Appl. No.: 14/493,469

(22) Filed: Sep. 23, 2014

(65) Prior Publication Data
US 2015/0086659 A1     Mar. 26, 2015

Related U.S. Application Data

(60) Provisional application No. 61/881,576, filed on Sep. 24, 2013.

(51) Int. Cl.
| | | |
|---|---|---|
| *A61K 8/02* | (2006.01) | |
| *A61Q 19/00* | (2006.01) | |
| *A61Q 19/10* | (2006.01) | |
| *A47L 13/17* | (2006.01) | |
| *B32B 5/02* | (2006.01) | |
| *B32B 5/26* | (2006.01) | |
| *B08B 1/00* | (2006.01) | |

(52) U.S. Cl.
CPC ............ *A61K 8/0208* (2013.01); *A47L 13/17* (2013.01); *A61Q 19/00* (2013.01); *A61Q 19/10* (2013.01); *B08B 1/006* (2013.01); *B32B 5/022* (2013.01); *B32B 5/26* (2013.01); *B32B 2262/0253* (2013.01); *B32B 2262/062* (2013.01); *B32B 2262/067* (2013.01); *B32B 2262/14* (2013.01); *B32B 2307/728* (2013.01); *B32B 2432/00* (2013.01); *B32B 2555/00* (2013.01)

(58) Field of Classification Search
CPC ....... A47L 13/17; A61K 8/0208; A61Q 19/00; A61Q 19/10; B08B 1/006; B32B 5/022; B32B 5/26; B32B 2262/0253; B32B 2262/062; B32B 2262/067; B32B 2262/14; B32B 2307/728; B32B 2432/00; B32B 2555/00
See application file for complete search history.

(56) References Cited

U.S. PATENT DOCUMENTS

| | | |
|---|---|---|
| 3,994,771 A | 11/1976 | Morgan et al. |
| 4,300,981 A | 11/1981 | Carstens |
| 5,143,679 A | 9/1992 | Weber et al. |
| 5,213,588 A | 5/1993 | Wong et al. |
| 5,518,801 A | 5/1996 | Chappell et al. |
| 5,628,097 A | 5/1997 | Benson et al. |
| 5,648,083 A | 7/1997 | Blieszner et al. |
| 5,658,639 A | 8/1997 | Curro et al. |
| 5,914,084 A | 6/1999 | Benson et al. |
| 5,916,661 A | 6/1999 | Benson et al. |
| 6,114,263 A | 9/2000 | Benson et al. |
| 6,129,801 A | 10/2000 | Benson et al. |
| 6,383,431 B1 | 5/2002 | Dobrin et al. |
| 7,005,557 B2 | 2/2006 | Klofta et al. |
| 7,666,827 B2 | 2/2010 | Marsh et al. |
| 8,221,774 B2 | 7/2012 | Marsh et al. |
| 2002/0128615 A1* | 9/2002 | Tyrrell ............... A61K 8/25 604/364 |
| 2004/0131820 A1 | 7/2004 | Turner et al. |
| 2004/0265534 A1 | 12/2004 | Curro et al. |
| 2005/0008680 A1 | 1/2005 | Deckner et al. |
| 2005/0008681 A1 | 1/2005 | Deckner et al. |
| 2005/0266055 A1 | 12/2005 | Stiller et al. |
| 2010/0256033 A1 | 10/2010 | Menard |
| 2011/0244199 A1 | 10/2011 | Brennan et al. |
| 2011/0268777 A1 | 11/2011 | Marsh et al. |
| 2012/0058165 A1* | 3/2012 | Klofta ............... D06M 15/285 514/782 |
| 2012/0066852 A1* | 3/2012 | Trinkaus ............ D04H 1/492 15/104.93 |
| 2012/0090112 A1 | 4/2012 | Carrier et al. |

FOREIGN PATENT DOCUMENTS

| | | |
|---|---|---|
| EP | 1140010 B1 | 11/2005 |
| JP | H09228213 A | 9/1997 |
| JP | 2006288604 A | 10/2006 |
| JP | 2008208491 A | 9/2008 |
| WO | 9700771 A1 | 1/1997 |
| WO | 02051456 A2 | 7/2002 |

OTHER PUBLICATIONS

International Search Report, PCT/US2014/056905, dated Nov. 28, 2014, 11 pages.

* cited by examiner

*Primary Examiner* — Matthew P Coughlin
*Assistant Examiner* — Thurman Wheeler
(74) *Attorney, Agent, or Firm* — Daniel S. Albrecht; Christian M. Best; Kathleen Yates Carter

(57) ABSTRACT

A wet wipe that exhibits a novel combination of properties and methods for making such wet wipes are provided.

13 Claims, 12 Drawing Sheets

WET WIPES COMPRISING A FIBROUS STRUCTURE AND A LIQUID COMPOSITION

FIELD

The present disclosure includes a wet wipe useful for cleaning soils from surfaces, such as skin, and delivering beneficial ingredients to the surface. A liquid composition may be incorporated into a fibrous structure to form a wet wipe for cleaning soils from surfaces and improving the wet wipe's tactile sensory characteristics.

BACKGROUND

Wet wipes may be useful for cleaning hard and soft surfaces. Wet wipes may also be useful for delivering functional materials to a surface. For example, a wet wipe may provide skin benefits, such as conditioning and/or moisturizing the skin, or protection from or treatment of diaper rash and other skin ailments such as eczema. Wet wipes may comprise a fibrous structure, generally a nonwoven material, and a liquid composition. The liquid composition may be predominately aqueous, in which the components are freely soluble or where those more lipophilic components are stably dispersed within the water. The liquid composition may be suitable for use on a variety of surfaces, including, for example, skin, wood, or countertops. For wet wipes used on skin, the liquid composition may comprise emulsifiers, emollients, skin care agents, pH buffers, solvents, preservatives, particles, metal sequestrants, anti-oxidants, perfumes, or other additives for cleaning and/or treating the skin.

Wet wipes, such as baby wipes for example, should be strong enough when combined with a liquid composition to maintain integrity in use and provide adequate cleaning performance, while also being soft enough to give a pleasing and comfortable tactile sensation to the user(s). Some wet wipes provide acceptable cleaning performance, but are rough to the touch. Other wet wipes are soft and gentle to the touch, but have poor cleaning performance. Therefore, it would be beneficial to provide a wipe that possesses both acceptable tactile sensations to the user as well as acceptable cleaning performance.

Moreover, some wet wipes may have a relatively large caliper to increase the thickness of the wipe and to increase the barrier between the soil and the user; however, the same wipes may be rough to the touch. Therefore, it would be beneficial to provide a wipe that has a relatively large caliper and that also provides acceptable tactile sensation to the user.

In addition, wet wipes should have sufficient absorbency to be effective in cleaning the soiled skin of a user while at the same time being sufficiently strong to protect the user from contacting the soil. Protecting the user from contacting the soil creates unique "barrier" demands for wipes that can negatively affect both the fibrous structures' absorbency and the tactile sensation of the wipe for the user. Moreover, wet wipes should have absorbency properties such that each wipe of a stack remains wet during extended storage periods.

Furthermore, wipes having a relatively large caliper and/or have good strength and cleaning performance may be stiff. Therefore, it would be beneficial to provide a wet wipe that has a high caliper, high strength, acceptable cleaning performance, while having acceptable tactile sensation, softness, and flexibility to the user.

Some wipes have the same properties on both sides of the wipe, including cleaning performance and tactile sensation. However, it may be beneficial to provide a wipe that has good cleaning performance on one side of the wipe and good tactile sensation on the other side of the wipe.

Some liquid compositions for wet wipes comprise an emollient. The emollient may maintain or improve the health of skin by delivering beneficial components to the skin, such as an omega-3, omega-6, omega-9 and other fatty acids which make up some vegetable oil triglycerides. However, adding an emollient to a liquid composition may result in a liquid composition having a greasy feel. Some consumers may prefer a liquid composition having some level of greasy feel, as the consumer may associate the greasy feel with a liquid composition that is gentle to the skin and/or provides benefits to the skin. On the other hand, some consumers may prefer a liquid composition that has little to no greasy feel, as the consumer may associate a greasy feel with a liquid composition that is not cleansing the skin as well and/or that is depositing unnecessary compounds to the skin. Sometimes, adding an emollient to a liquid composition may also result in a slimy feel to the wet wipe. Therefore, it would be beneficial to provide a liquid composition comprising an emollient in the form of an emulsion that has a good tactile sensation to the user.

Accordingly, there is a need for wipes that exhibit a satisfactory level of cleaning performance coupled with user-acceptable tactile sensation, a high degree of absorbency, barrier protection, stable moisture distribution in a stack, a large caliper, acceptable flexibility, and/or strength in use.

SUMMARY

Aspects of the present disclosure include a wet wipe comprising a fibrous structure. The fibrous structure comprises filaments and solid additives. The wet wipe further comprises a liquid composition. The wet wipe exhibits a Tactile Sensory Coefficient of Friction of less than 0.60 as measured according to the Tactile Sensory Coefficient of Friction Test Method described herein. The fibrous structure may have a Liquid Absorptive Capacity of greater than 12 g/g as measured according to the Liquid Absorptive Capacity Test Method described herein. The wet wipe may have a caliper of greater than about 0.1 millimeters. The wet wipe may have a Wet to Dry Drape Ratio of less than about 0.80 measured according to the Wet to Dry Drape Ratio Test Method described herein. The wet wipe may have a Cleaning Coefficient of Friction of greater than 0.40 measured according to the Cleaning Coefficient of Friction Test Method described herein. The wet wipe may have a Compressive Modulus of greater than about 4.75 [log(gsi)] measured according to the Compressive Modulus Test Method described herein.

Aspects of the present disclosure include a wet wipe comprising a fibrous structure and a liquid composition. The liquid composition comprises an emollient. The wet wipe exhibits a Cleaning Coefficient of Friction of greater than 0.40 as measured according to the Cleaning Coefficient of Friction Test Method described herein. The liquid composition may comprise from about 0.1% % to about 5% of the emollient based upon the total weight of the liquid composition.

The fibrous structure may have a Liquid Absorptive Capacity of greater than 12 g/g as measured according to the Liquid Absorptive Capacity Test Method described herein. The wet wipe may have a caliper of greater than about 0.1 millimeters. The wet wipe may have a Wet to Dry Drape Ratio of less than about 0.80 measured according to the Wet to Dry Drape Ratio Test Method described herein. The wet wipe may have a Tactile Sensory Coefficient of Friction of less than 0.60 measured according to the Tactile Sensory Coefficient of Friction Test Method described herein. The wet wipe may have a Compressive Modulus of greater than about 4.75 [log(gsi)] measured according to the Compressive Modulus Test Method described herein.

Aspects of the present disclosure include a wet wipe comprising a fibrous structure and a liquid composition, wherein the wet wipe exhibits a Wet to Dry Drape Ratio of less than about 0.80 as measured according to the Wet to Dry Drape Ratio Test Method described herein. The fibrous structure may have a Liquid Absorptive Capacity of greater than 12 g/g as measured according to the Liquid Absorptive Capacity Test Method described herein. The wet wipe may have a caliper of greater than about 0.1 millimeters. The wet wipe may have a Tactile Sensory Coefficient of Friction of less than 0.60 measured according to the Tactile Sensory Coefficient of Friction Test Method described herein. The wet wipe may have a Cleaning Coefficient of Friction of greater than 0.40 measured according to the Cleaning Coefficient of Friction Test Method described herein. The wet wipe may have a Compressive Modulus of greater than about 4.75 [log(gsi)] measured according to the Compressive Modulus Test Method described herein.

Aspects of the present disclosure include a wet wipe comprising a fibrous structure and a liquid composition, wherein the wet wipe exhibits a Compressive Modulus of greater than about 4.75 [log(gsi)] measured according to the Compressive Modulus Test Method described herein. The fibrous structure may have a Liquid Absorptive Capacity of greater than 12 g/g as measured according to the Liquid Absorptive Capacity Test Method described herein. The wet wipe may have a caliper of greater than about 0.1 millimeters. The wet wipe may have a Tactile Sensory Coefficient of Friction of less than 0.60 measured according to the Tactile Sensory Coefficient of Friction Test Method described herein. The wet wipe may have a Cleaning Coefficient of Friction of greater than 0.40 measured according to the Cleaning Coefficient of Friction Test Method described herein. The wet wipe may have a Wet to Dry Drape Ratio of less than about 0.8 measured according to the Wet to Dry Drape Ratio Test Method described herein.

Aspects of the present disclosure include a wet wipe comprising a fibrous structure, wherein the fibrous structure comprises filaments and solid additives. The wet wipe further comprises a liquid composition, wherein the liquid composition comprises an emollient and a clay mineral.

The weight ratio of emollient to clay mineral present in the liquid composition is in the range of about 1:30 to about 30:1.

The liquid composition further comprises a rheology modifier, wherein the weight ratio of emollient to rheology modifier present in the liquid composition is in the range of about 1:20 to about 60:1. The rheology modifier may comprise xanthan gum and a clay mineral.

The liquid composition may comprise from about 0.1% % to about 3%, based on the total weight of the liquid composition, of the emollient.

The liquid composition may have a peak complex viscosity in the range of about 50 mPas to about 2000 mPas according to the Peak Complex Viscosity Test Method.

The liquid composition may comprise an emulsifier. The emulsifier may comprise sodium stearate, glycerol stearate citrate, and glyceryl stearate.

The liquid composition has a pH in the range of about 3.5 to about 5.5.

The wet wipe may comprise from about 200% % to about 500%, based on the total weight of the fibrous structure, of the liquid composition.

The fibrous structure may have a Liquid Absorptive Capacity of greater than 12 g/g as measured according to the Liquid Absorptive Capacity Test Method described herein. The wet wipe may have a caliper of greater than about 0.1 millimeters. The wet wipe may have a Tactile Sensory Coefficient of Friction of less than 0.60 measured according to the Tactile Sensory Coefficient of Friction Test Method described herein. The wet wipe may have a Cleaning Coefficient of Friction of greater than 0.40 measured according to the Cleaning Coefficient of Friction Test Method described herein. The wet wipe may have a Wet to Dry Drape Ratio of less than about 0.8 measured according to the Wet to Dry Drape Ratio Test Method described herein. The wet wipe may have a Compressive Modulus of greater than about 4.75 [log(gsi)] measured according to the Compressive Modulus Test Method described herein.

At least one of the solid additives may comprise a fiber. The fiber may comprise a wood pulp fiber. The wood pulp fiber may be selected from the group consisting of: treated or untreated softwood fibers like Southern Softwood Kraft pulp fibers, Northern Softwood Kraft pulp fibers, treated or untreated hardwood fibers like *Eucalyptus* pulp fibers, *Acacia* pulp fibers, and combinations thereof. For example, the wood fibers might be chemically treated to reduce the defiberization energy required to break up the sheets of dry wood pulp into individual wood fibers.

At least one of the filaments may comprise a thermoplastic polymer. The thermoplastic polymer may be selected from the group consisting of: polypropylene, polyethylene, polyester, polylactic acid, polyhydroxyalkanoate, polyvinyl alcohol, polycaprolactone and mixtures thereof. At least one of the filaments may a natural polymer. The natural polymer may be selected from the group consisting of: starch, starch derivatives, cellulose, cellulose derivatives, hemicellulose, hemicellulose derivatives and mixtures thereof. At least one surface of the fibrous structure may comprise a layer of filaments.

DETAILED DESCRIPTION

Figure 1:
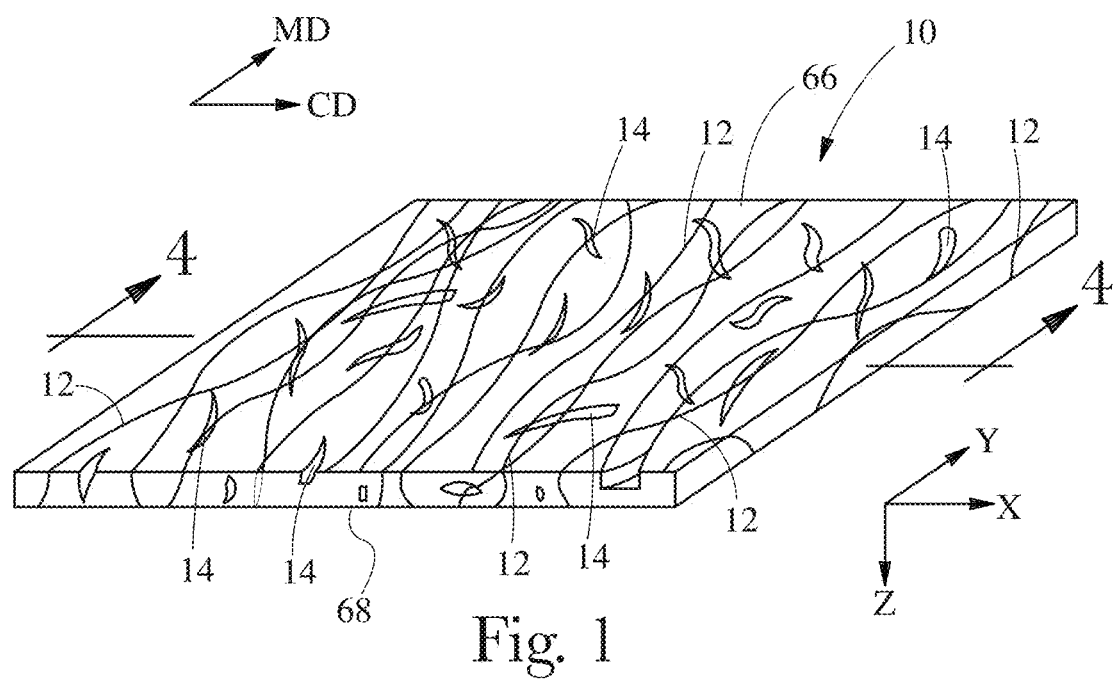
FIG. 1 is a schematic representation of an example of a fibrous structure according to the present invention.

The following definitions may be useful in understanding the present disclosure.

"Loading" refers to a process of applying a liquid composition to a fibrous structure to form a wet wipe. A "loaded" fibrous structure is associated with a liquid composition.

"Soil" refers herein to matter that is extraneous to a surface being cleaned. For example, soils include body exudates, household matter, and outdoor matter. Body exudates include feces, menses, urine, vomitus, mucus, combinations thereof, and the like. Household matter includes food, beverages, paint, crayons, combinations thereof, and the like. Outdoor matter includes dirt, mud, snow, combinations thereof, and the like.

"Q.S." refers herein to "quantum sufficit" and is a sufficient percentage of water added to the composition to bring the overall composition to 100%.

Values disclosed herein as ends of ranges are not to be understood as being strictly limited to the exact numerical values recited. Instead, unless otherwise specified, each numerical range is intended to mean both the recited values and any integers within the range. For example a range disclosed as "1 to 10" is intended to mean "1, 2, 3, 4, 5, 6, 7, 8, 9, and 10".

As used herein, the articles "a" and "an" when used herein, for example, "an anionic surfactant" or "a fiber" is understood to mean one or more of the material that is claimed or described.

"Machine direction" (MD) is used herein to refer to the direction of material flow through a process for making a fibrous structure. In addition, relative placement and movement of material can be described as flowing in the machine direction through a process from upstream in the process to downstream in the process. "Cross direction" (CD) is used herein to refer to a direction that is not parallel with, and usually perpendicular to, the machine direction.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

The present disclosure includes wet wipes, and, more particularly, includes wet wipes comprising a fibrous structure in combination with a liquid composition. Fibrous structures of the present disclosure may include filaments and/or solid additives. It has surprisingly been found that the fibrous structure of the present invention exhibit a Sensory Tactile Coefficient of Friction lower than other known fibrous substrates comprising filaments and solid additives as measured according to the Sensory Tactile Coefficient of Friction Test Method.

Some consumers prefer a wet wipe to be soft such that the wet wipe provides a pleasing and comfortable tactile sensation when the user is holding and/or using the wipe to clean a surface. Without wishing to be bound by theory, it is believed that the Sensory Tactile Coefficient of Friction Test Method provides a coefficient of friction value that directly correlates with a user's tactile sensation as the user is holding the wipe and/or using the wipe to clean a surface. For example, it is believed that a relatively high Sensory Tactile Coefficient of Friction correlates with a wet wipe that feels rough, and, therefore, provides an uncomfortable tactile sensation to the user. On the other hand, it is believed that a relatively low Sensory Tactile Coefficient of Friction correlates with a wet wipe that feels soft, and, therefore, provides a comfortable tactile sensation to the user.

The present disclosure includes liquid compositions comprising an emollient. A liquid composition comprising an emollient may be useful for improving and/or maintaining skin health. In particular, a liquid composition comprising an emollient may deliver beneficial compounds, such as essential fatty acids, to the skin. In addition, the emollient may soothe, soften, protect, moisturize, heal, or otherwise improve the condition and/or appearance of the skin. Furthermore, natural emollients may be selected, which may appeal to users who are concerned about the health effects of synthetic compounds. However, incorporating an emollient into an aqueous liquid composition can be difficult. Moreover, incorporating an emollient into an aqueous composition may have negative tactile sensation for some consumers, as the liquid composition may feel too greasy, slippery, sticky, and/or slimy.

Liquid compositions of the present disclosure may comprise an emollient in combination with a mineral such as a clay mineral. It has been found that a liquid composition comprising a level of emollient sufficient to deliver beneficial compounds to the skin in combination with a clay mineral has little to no greasy, slippery, and/or slimy feel. Without wishing to be bound by theory, it is believed that a clay mineral reduces the greasy, slippery, and/or slimy feel of the emollient by introducing a more powdery feel that works in synergy with the emollient to make a more preferred tactile sensory experience for users. Moreover, a liquid composition comprising an emollient and a clay mineral has acceptable stability for use in a wet wipe. Additionally, it has been found that a liquid composition comprising an emollient, a clay mineral, and a rheology modifier may further reduce the greasy, slippery, sticky and/or slimy feel of some emollients and some rheology modifiers to produce a more preferred tactile sensory experience for caregivers, while minimizing the amount of clay mineral that is needed in the liquid composition. In some instances, it has been found that only a mineral such as a clay mineral is needed to reduce the greasy, slippery, sticky and/or slimy feel of the lotion composition.

It has surprisingly been found that the wet wipes of the present disclosure exhibit a Cleaning Coefficient of Friction higher than other known wet wipes comprising fibrous substrates having filaments and solid additives and liquid compositions comprising an emollient and/or clay mineral as measured according to the Cleaning Coefficient of Friction Test Method.

For a wet wipe that is being used to clean a surface, users prefer the wet wipe to not only provide a good sensory perception, but users also prefer that the wet wipe to have excellent cleaning performance. Without wishing to be bound by theory, it is believed that the Cleaning Coefficient of Friction Test Method provides a coefficient of friction value that directly correlates with a wet wipe's ability to clean a surface. For example, it is believed that a relatively high Cleaning Coefficient of Friction correlates with a wet wipe that has excellent cleaning performance, and, therefore, is positively perceived by a user. On the other hand, it is believed that a relatively low Cleaning Coefficient of Friction correlates with a wet wipe that has poor cleaning performance, and, therefore, is negatively perceived by a consumer.

It has surprisingly been found that wet wipes of the present disclosure exhibit a user acceptable Cleaning Coefficient of Friction and a user acceptable Tactile Sensation Coefficient of Friction. Without wishing to be bound by theory, wet wipes of the present disclosure may also exhibit a relatively high Caliper and high Compressive Modulus, which may correlate with a user acceptable level of strength and barrier protection between the user and the soil being removed from the surface. A high Compressive Modulus may also correlate with less deformation of the wet wipe during processing and handling of the wet wipes. In turn, the processability of the wipe may be enhanced as friction between the wipe and the processing equipment may allow the wipe to advance through the processing equipment without having to significantly deform the wipes. Wet wipes of the present disclosure may also exhibit a relatively high Liquid Absorptive Capacity, which may correlate with improved cleaning. Moreover, wet wipes of the present disclosure may have acceptable saturation properties such that each wipe of a stack remains wet during extended storage periods. Wet wipes of the present disclosure may exhibit a relatively low Drape Ratio such that the liquid composition of the wet wipe may significantly reduce the drape of the wet wipe from a dry state to a wet state. As a result of a relatively low Drape Ratio, the wet wipe may exhibit a relatively high degree of flexibility and/or softness.

Wet wipes of the present disclosure may have different properties on different sides of the wet wipe. For example, one side of the wipe may have good cleaning performance and the other side of the wet wipe may have good tactile sensation to the user. In another example, one side of the wet wipe may have an increased cleaning performance as compared to the other side of the wet wipe.

While the present disclosure references the use of a wet wipe for cleaning skin, it is to be appreciated that the wet wipes of the present disclosure may be used to clean various other surfaces other than skin, including countertops, walls, floors, appliances, furniture, and the like.

Fibrous Structure

"Fibrous structure" as used herein means a structure that comprises one or more filaments and/or fibers. In one example, the fibrous structure is a wipe, such as a wet wipe, for example a baby wipe. For example, "fibrous structure" and "wipe" may be used interchangeably herein. In one example, a fibrous structure according to the present disclosure means an orderly arrangement of filaments and/or fibers within a structure in order to perform a function. In another example, a fibrous structure according to the present disclosure is a nonwoven.

Non-limiting examples of processes for making fibrous structures include known wet-laid papermaking processes, air-laid papermaking processes including carded and/or spunlaced processes. Such processes typically include steps of preparing a fiber composition in the form of a suspension in a medium, either wet, more specifically aqueous medium, or dry, more specifically gaseous, i.e. with air as medium. The aqueous medium used for wet-laid processes is oftentimes referred to as a fiber slurry. The fibrous slurry is then used to deposit a plurality of fibers onto a forming wire or belt such that an embryonic fibrous structure is formed, after which drying and/or bonding the fibers together results in a fibrous structure. Further processing the fibrous structure may be carried out such that a finished fibrous structure is formed. For example, in typical papermaking processes, the finished fibrous structure is the fibrous structure that is wound on the reel at the end of papermaking, and may subsequently be converted into a finished product, e.g. a sanitary tissue product.

The fibrous structures of the present disclosure may be homogeneous or may be layered. If layered, the fibrous structures may comprise at least two and/or at least three and/or at least four and/or at least five layers.

In one example the fibrous structure is a nonwoven.

"Nonwoven" for purposes of the present disclosure as used herein and as defined by EDANA means a sheet of fibers, continuous filaments, or chopped yarns of any nature or origin, that have been formed into a web by any means, and bonded together by any means, with the exception of weaving or knitting. Felts obtained by wet milling are not nonwovens. Wetlaid webs are nonwovens provided that they contain a minimum of 50% by weight of man-made fibers, filaments or other fibers of non-vegetable origin with a length to diameter ratio that equals or exceeds 300 or a minimum of 30% by weight of man-made fibers, filaments or other fibers of non-vegetable origin with a length to diameter ratio that equals or exceeds 600 and a maximum apparent density of 0.40 g/cm$^3$.

The fibrous structures of the present disclosure may be co-formed fibrous structures.

"Co-formed fibrous structure" as used herein means that the fibrous structure comprises a mixture of at least two different materials wherein at least one of the materials comprises a filament, such as a polypropylene filament, and at least one other material, different from the first material, comprises a solid additive, such as a fiber and/or a particulate. In one example, a co-formed fibrous structure comprises solid additives, such as fibers, such as wood pulp fibers and/or absorbent gel materials and/or filler particles and/or particulate spot bonding powders and/or clays, and filaments, such as polypropylene filaments.

"Solid additive" as used herein means a fiber and/or a particulate.

"Particulate" as used herein means a granular substance or powder.

"Fiber" and/or "Filament" as used herein means an elongate particulate having an apparent length greatly exceeding its apparent width, i.e. a length to diameter ratio of at least about 10. For purposes of the present disclosure, a "fiber" is an elongate particulate as described above that exhibits a length of less than 5.08 cm (2 in.) and a "filament" is an elongate particulate as described above that exhibits a length of greater than or equal to 5.08 cm (2 in.).

Fibers are typically considered discontinuous in nature. Non-limiting examples of fibers include wood pulp fibers; rayon, which in turn includes but is not limited to viscose, lyocell, cotton; wool; silk; jute; linen; ramie; hemp; flax; camel hair; kenaf; and synthetic staple fibers made from polyester, nylons, polyolefins such as polypropylene, polyethylene, natural polymers, such as starch, starch derivatives, cellulose and cellulose derivatives, hemicellulose, hemicellulose derivatives, chitin, chitosan, polyisoprene (cis and trans), peptides, polyhydroxyalkanoates, copolymers of polyolefins such as polyethylene-octene, and biodegradable or compostable thermoplastic fibers such as polylactic acid filaments, polyvinyl alcohol filaments, and polycaprolactone filaments. The fibers may be monocomponent or multicomponent, such as bicomponent filaments, round, non-round fibers; and combinations thereof.

Filaments are typically considered continuous or substantially continuous in nature. Filaments are relatively longer than fibers. Non-limiting examples of filaments include meltblown and/or spunbond filaments. Non-limiting examples of materials that can be spun into filaments include natural polymers, such as starch, starch derivatives, cellulose and cellulose derivatives, hemicellulose, hemicellulose derivatives, chitin, chitosan, polyisoprene (cis and trans), peptides, polyhydroxyalkanoates, and synthetic polymers including, but not limited to, thermoplastic polymer filaments comprising thermoplastic polymers, such as polyesters, nylons, polyolefins such as polypropylene filaments, polyethylene filaments, polyvinyl alcohol and polyvinyl alcohol derivatives, sodium polyacrylate (absorbent gel material) filaments, and copolymers of polyolefins such as polyethylene-octene, and biodegradable or compostable thermoplastic fibers such as polylactic acid filaments, polyvinyl alcohol filaments, and polycaprolactone filaments. The filaments may be monocomponent or multicomponent, such as bicomponent filaments.

In one example of the present disclosure, "fiber" refers to papermaking fibers. Papermaking fibers useful in the present disclosure include cellulosic fibers commonly known as wood pulp fibers such as those derived from softwood trees or hardwood trees. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. U.S. Pat. Nos. 4,300,981 and 3,994,771 are incorporated herein by reference for the purpose of disclosing layering of hardwood and softwood fibers. Also applicable to the present disclosure are fibers derived from recycled paper, which may contain any or all of the above categories as well as other non-fibrous materials such as fillers and adhesives used to facilitate the original papermaking.

In addition to the various wood pulp fibers, other cellulosic fibers such as cotton linters, rayon, lyocell and bagasse can be used with the present disclosure. Other sources of cellulose in the form of fibers or capable of being spun into fibers include grasses and grain sources.

"Sanitary tissue product" as used herein means a soft, low density (i.e. <about 0.15 g/cm$^3$) web useful as a wiping implement for post-urinary and post-bowel movement cleaning (toilet tissue), for otorhinolaryngological discharges (facial tissue), and multi-functional absorbent and cleaning uses (absorbent towels). Non-limiting examples of suitable sanitary tissue products of the present disclosure include paper towels, bath tissue, facial tissue, napkins, baby wipes, adult wipes, wet wipes, cleaning wipes, polishing wipes, cosmetic wipes, car care wipes, wipes that comprise an active agent for performing a particular function, cleaning fibrous structures for use with implements, such as a SWIFFER® cleaning wipe/pad. The sanitary tissue product may be convolutedly wound upon itself about a core or without a core to form a sanitary tissue product roll.

In one example, the sanitary tissue product of the present disclosure comprises a fibrous structure according to the present disclosure.

The sanitary tissue products of the present disclosure may exhibit a basis weight between about 10 g/m$^2$ to about 120 g/m$^2$ and/or from about 15 g/m$^2$ to about 110 g/m$^2$ and/or from about 20 g/m$^2$ to about 100 g/m$^2$ and/or from about 30 to 90 g/m$^2$. In addition, the sanitary tissue product of the present disclosure may exhibit a basis weight between about 40 g/m$^2$ to about 120 g/m$^2$ and/or from about 50 g/m$^2$ to about 110 g/m$^2$ and/or from about 55 g/m$^2$ to about 105 g/m$^2$ and/or from about 60 to 100 g/m$^2$.

The sanitary tissue products of the present disclosure may exhibit a density (measured at 95 g/in$^2$) of less than about 0.60 g/cm$^3$ and/or less than about 0.30 g/cm$^3$ and/or less than about 0.20 g/cm$^3$ and/or less than about 0.10 g/cm$^3$ and/or less than about 0.07 g/cm$^3$ and/or less than about 0.05 g/cm$^3$ and/or from about 0.01 g/cm$^3$ to about 0.20 g/cm$^3$ and/or from about 0.02 g/cm$^3$ to about 0.10 g/cm$^3$.

The sanitary tissue products of the present disclosure may comprises additives such as softening agents, temporary wet strength agents, opacifiers, preservatives, anti-oxidants, colorants, permanent wet strength agents, bulk softening agents, silicones, wetting agents, latexes, especially surface-pattern-applied latexes, dry strength agents such as carboxymethylcellulose and starch, and other types of additives suitable for inclusion in and/or on sanitary tissue products.

"Weight average molecular weight" as used herein means the weight average molecular weight as determined using gel permeation chromatography according to the protocol found in Colloids and Surfaces A. Physico Chemical & Engineering Aspects, Vol. 162, 2000, pg. 107-121.

"Basis Weight" as used herein is the weight per unit area of a sample reported in lbs/3000 ft$^2$ or g/m$^2$ (gsm).

"Stack" as used herein, refers to a neat pile of fibrous structures and/or wipes. Based upon the assumption that there are at least three wipes in a stack, each wipe, except for the topmost and bottommost wipes in the stack, will be directly in face to face contact with the wipe directly above and below itself in the stack. Moreover, when viewed from above, the wipes will be layered on top of each other, or superimposed, such that only the topmost wipe of the stack will be visible. The height of the stack is measured from the bottom of the bottommost wipe in the stack to the top of the topmost wipe in the stack and is provided in units of millimeters (mm).

When present on or in the fibrous structure, the liquid composition may be present at a level of from about 10% to about 1000% of the basis weight of the fibrous structure and/or from about 100% to about 700% of the basis weight of the fibrous structure and/or from about 200% to about 500% and/or from about 200% to about 400% of the basis weight of the fibrous structure.

"Wet" refers to fibrous structures and/or wipes which are moistened with a liquid composition prior to packaging in a generally moisture impervious container or wrapper. Such wet wipes, which can also be referred to in commerce as "towelettes" or "pre-moistened wipes", may be suitable for use in cleaning babies, as well as older children and adults.

"Saturation loading" and "lotion loading" are used interchangeably herein and refer to the amount of liquid composition applied to the fibrous structure or wipe. In general, the amount of liquid composition applied may be chosen in order to provide maximum benefits to the end product comprised by the wipe. Saturation loading is typically expressed as grams of liquid composition per gram of dry wipe substrate.

Saturation loading, often expressed as percent saturation, is defined as the percentage of the dry fibrous structure or wipe's mass (void of any liquid composition) that a liquid composition present on/in the fibrous structure or wipe represents. For example, a saturation loading of 1.0 (equivalently, 100% saturation) indicates that the mass of liquid composition present on/in the fibrous structure or wipe is equal to the mass of dry fibrous structure or wipe (void of any liquid composition).

The following equation is used to calculate saturation load of a fibrous structure or wipe:

$$\text{Saturation Loading} = \left[\frac{\text{wet wipe mass}}{(\text{wipe size}) * (\text{basis weight})}\right] - 1$$

"Saturation gradient index" (SGI) is a measure of how well the wipes at the top of a stack retain moisture. The SGI of a stack of wipes is measured as described above and is calculated as the ratio of the average lotion load of the bottommost wipes in the stack versus the topmost wipes in the stack. The ideal stack of wipes will have an SGI of about 1.0; that is, the topmost wipes will be equally as moist as the bottommost wipes. In the aforementioned exemplary configurations, the stacks have a SGI from about 1.0 to about 1.5.

The saturation gradient index for a fibrous structure or wipe stack is calculated as the ratio of the saturation loading of a set number of fibrous structures or wipes from the bottom of a stack to that of the same number of fibrous structures or wipes from the top of the stack. For example, for an approximately 80 count wipe stack, the saturation gradient index is this ratio using 10 wipes from bottom and top; for an approximately 30 count wipe stack, 5 wipes from bottom and top are used; and for less than 30, only the top and bottom single wipes are used in the saturation gradient index calculation. The saturation gradient index for a wipe stack is performed at least seven days after the wipe stack is produced. The following equation illustrates the example of an 80 count stack saturation gradient index calculation:

$$\text{Saturation Gradient Index} = \frac{\text{average lotion load of bottom 10 wipes in stack}}{\text{average lotion load of top 10 wipes in stack}}$$

A saturation profile, or wetness gradient, exists in the stack when the saturation gradient index is greater than 1.0. In cases where the saturation gradient index is significantly greater than 1.0, e.g. over about 1.5, lotion is draining from the top of the stack and settling in the bottom of the container, such that there may be a noticeable difference in the wetness of the topmost fibrous structures or wipes in the stack compared to that of the fibrous structures or wipes nearest the bottom of the stack. For example, a perfect tub of wipes would have a saturation gradient index of 1.0; the bottommost wipes and topmost wipes would maintain equivalent saturation loading during storage. Additional liquid composition would not be needed to supersaturate the wipes in an effort to keep all of the wipes moist, which typically results in the bottommost wipes being soggy.

"Percent moisture" or "% moisture" or "moisture level" as used herein means 100×(the ratio of the mass of water contained in a fibrous structure to the mass of the fibrous structure). The product of the above equation is reported as a %.

"Surface tension" as used herein, refers to the force at the interface between a liquid composition and air. Surface tension is typically expressed in dynes per centimeter (dynes/cm).

"Visible" as used herein, refers to being capable of being seen by the naked eye when viewed at a distance of 12 inches (in), or 30.48 centimeters (cm), under the unimpeded light of an ordinary incandescent 60 watt light bulb that is inserted in a fixture such as a table lamp. It follows that "visually distinct" as used herein refers to those features of nonwoven wipes, whether or not they are wet, that are readily visible and discernable when the wipe is subjected to normal use, such as the cleaning of a child's skin.

"Ply" as used herein means an individual, integral fibrous structure.

"Plies" as used herein means two or more individual, integral fibrous structures disposed in a substantially contiguous, face-to-face relationship with one another, forming a multi-ply fibrous structure and/or multi-ply sanitary tissue product. It is also contemplated that an individual, integral fibrous structure can effectively form a multi-ply fibrous structure, for example, by being folded on itself.

Figure 2:
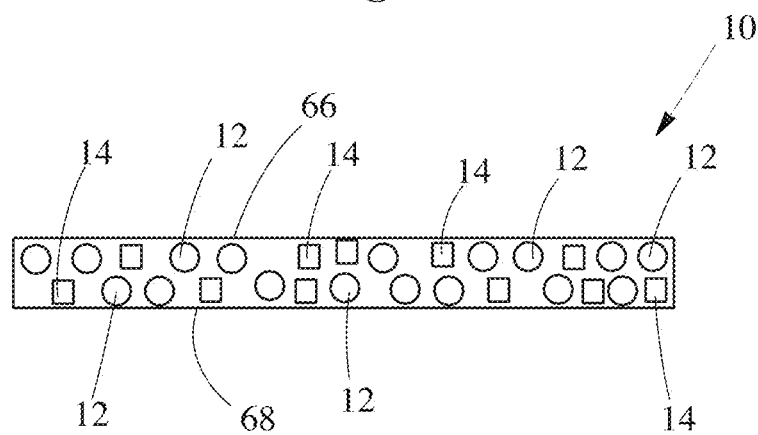
FIG. 2 is a schematic, cross-sectional representation of FIG. 1 taken along line 2-2.

FIGS. 1 and 2 show schematic representations of an example of a fibrous structure in accordance with the present disclosure. As shown in FIGS. 1 and 2, the fibrous structure 10 may be a co-formed fibrous structure. The fibrous structure 10 comprises a plurality of filaments 12, such as polypropylene filaments, and a plurality of solid additives, such as wood pulp fibers 14. The filaments 12 may be randomly arranged as a result of the process by which they are spun and/or formed into the fibrous structure 10. The wood pulp fibers 14, may be randomly dispersed throughout the fibrous structure 10 in the x-y plane. The wood pulp fibers 14 may be non-randomly dispersed throughout the fibrous structure in the z-direction. In one example (not shown), the wood pulp fibers 14 are present at a higher concentration on one or more of the exterior, x-y plane surfaces than within the fibrous structure along the z-direction. As shown in FIGS. 1 and 2, the fibrous structure 10 may be in the form of a wet wipe having a first side 66 and a second side 68.

Figure 3:
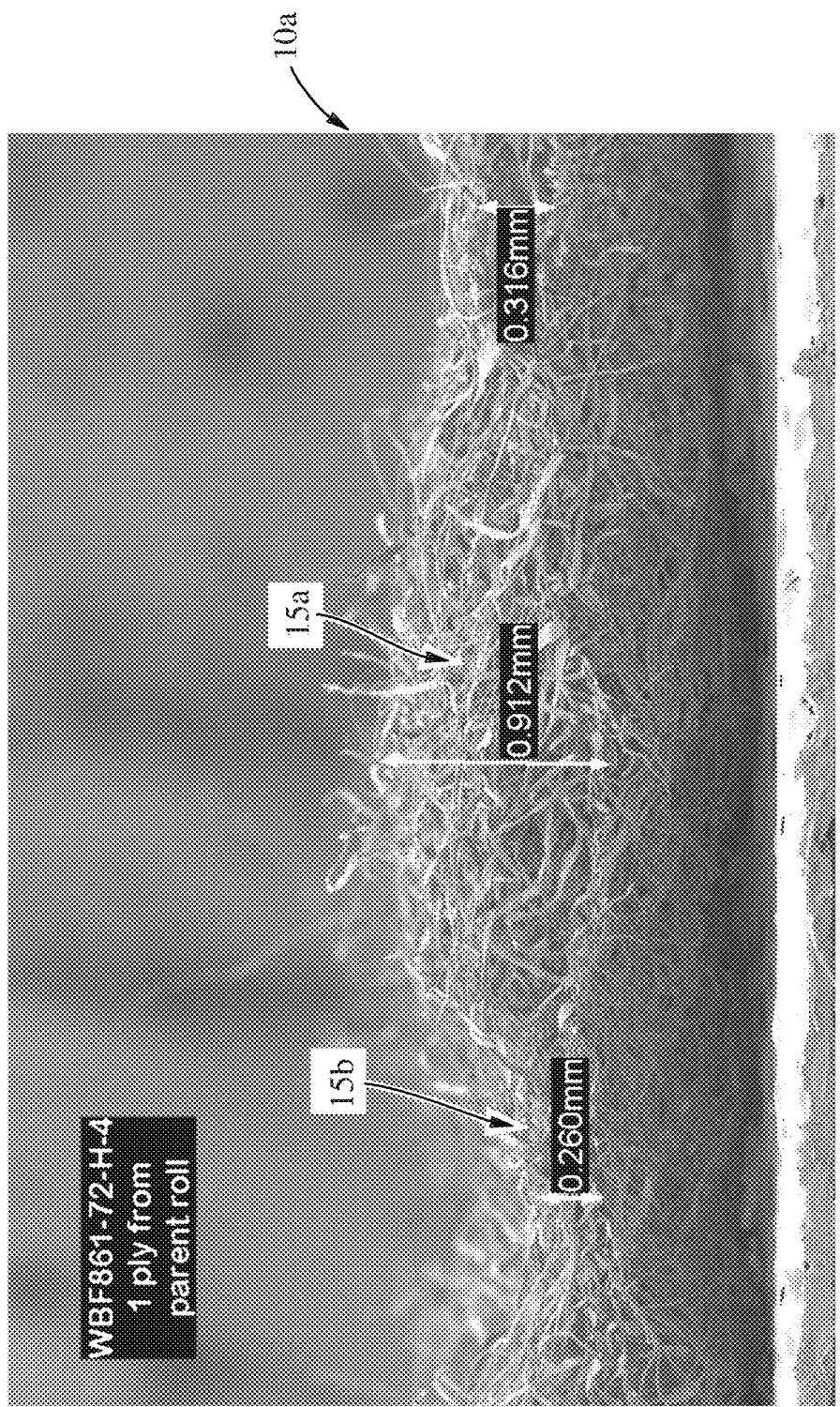
FIG. 3 is a scanning electromicrophotograph of a cross-section of another example of fibrous structure according to the present invention.

FIG. 3 shows a cross-sectional, SEM microphotograph of another example of a fibrous structure 10a in accordance with the present disclosure shows a fibrous structure 10a comprising a non-random, repeating pattern of microregions 15a and 15b. The microregion 15a (typically referred to as a "pillow") exhibits a different value of a common intensive property than microregion 15b (typically referred to as a "knuckle"). In one example, the microregion 15b is a continuous or semi-continuous network and the microregion 15a are discrete regions within the continuous or semi-continuous network. The common intensive property may be caliper. In another example, the common intensive property may be density.

Figure 4:
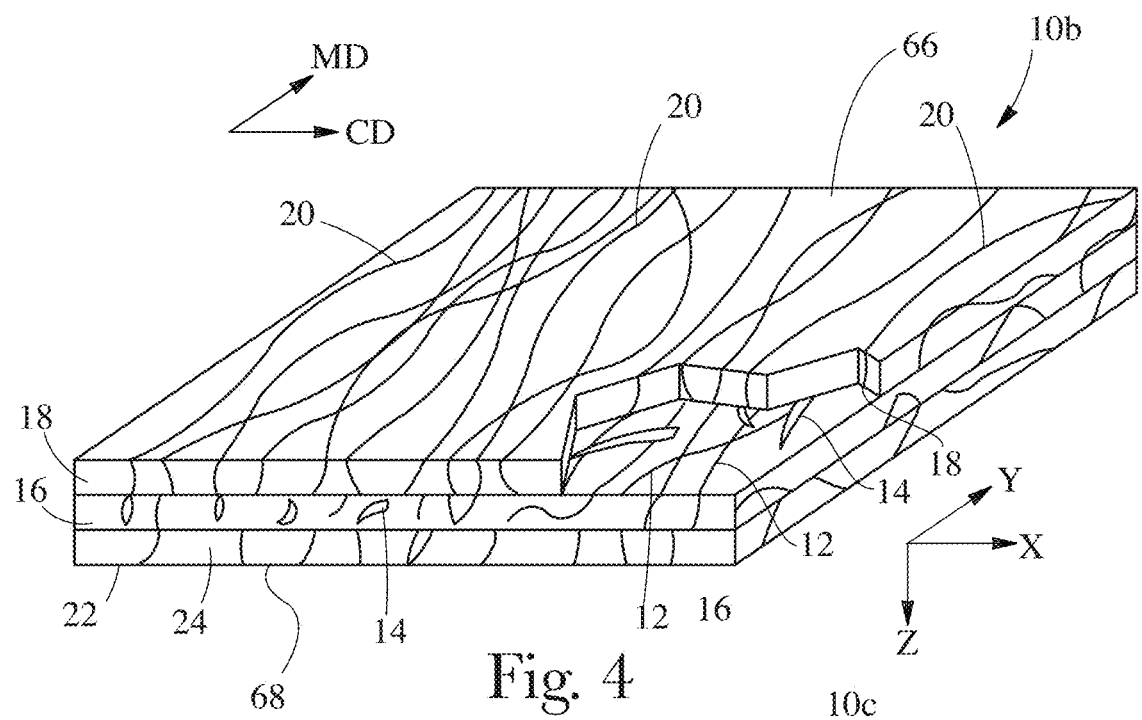
FIG. 4 is a schematic representation of another example of a fibrous structure according to the present invention.

As shown in FIG. 4, another example of a fibrous structure in accordance with the present disclosure is a layered fibrous structure 10b. The layered fibrous structure 10b comprises a first layer 16 comprising a plurality of filaments 12, such as polypropylene filaments, and a plurality of solid additives, in this example, wood pulp fibers 14. The layered fibrous structure 10b further comprises a second layer 18 comprising a plurality of filaments 20, such as polypropylene filaments. In one example, the first and second layers 16, 18, respectively, are sharply defined zones of concentration of the filaments and/or solid additives. The plurality of filaments 20 may be deposited directly onto a surface of the first layer 16 to form a layered fibrous structure that comprises the first and second layers 16, 18, respectively.

Further, the layered fibrous structure 10b may comprise a third layer 22, as shown in FIG. 4. The third layer 22 may comprise a plurality of filaments 24, which may be the same or different from the filaments 20 and/or 16 in the second 18 and/or first 16 layers. As a result of the addition of the third layer 22, the first layer 16 is positioned, for example sandwiched, between the second layer 18 and the third layer 22. The plurality of filaments 24 may be deposited directly onto a surface of the first layer 16, opposite from the second layer, to form the layered fibrous structure 10b that comprises the first, second and third layers 16, 18, 22, respectively.

Figure 5:
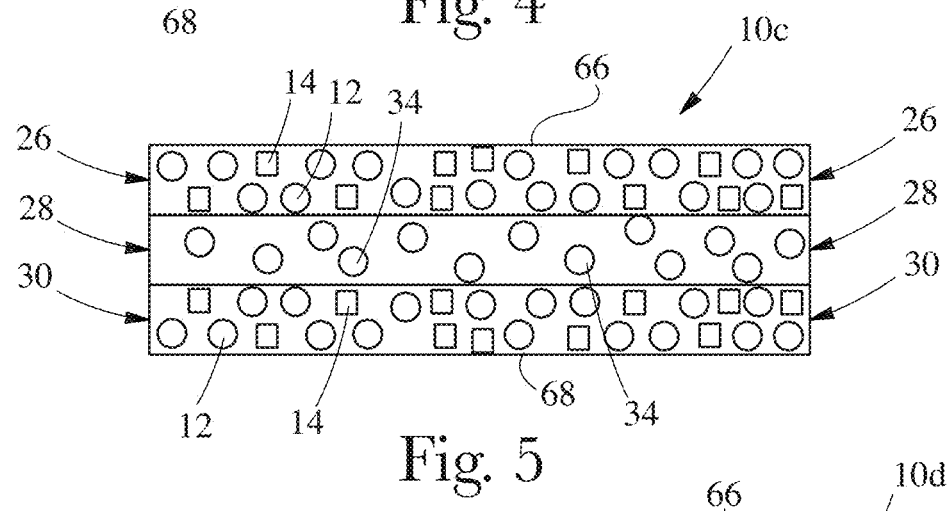
FIG. 5 is a schematic, cross-sectional representation of another example of a fibrous structure according to the present invention.

As shown in FIG. 5, a cross-sectional schematic representation of another example of a fibrous structure in accordance with the present disclosure comprising a layered fibrous structure 10c is provided. The layered fibrous structure 10c comprises a first layer 26, a second layer 28 and optionally a third layer 30. The first layer 26 comprises a plurality of filaments 12, such as polypropylene filaments, and a plurality of solid additives, such as wood pulp fibers 14. The second layer 28 may comprise any suitable filaments, solid additives and/or polymeric films. In one example, the second layer 28 comprises a plurality of filaments 34. In one example, the filaments 34 comprise a polymer selected from the group consisting of: polysaccharides, polysaccharide derivatives, polyvinylalcohol, polyvinylalcohol derivatives and mixtures thereof.

In yet another example, a fibrous structure of the present disclosure may comprise two outer layers consisting of 100% by weight filaments and an inner layer consisting of 100% by weight fibers.

In another example of a fibrous structure in accordance with the present disclosure, instead of being layers of fibrous structure 10c, the material forming layers 26, 28 and 30, may be in the form of plies wherein two or more of the plies may be combined to form a fibrous structure. The plies may be bonded together, such as by thermal bonding and/or adhesive bonding, to form a multi-ply fibrous structure.

Figure 6:
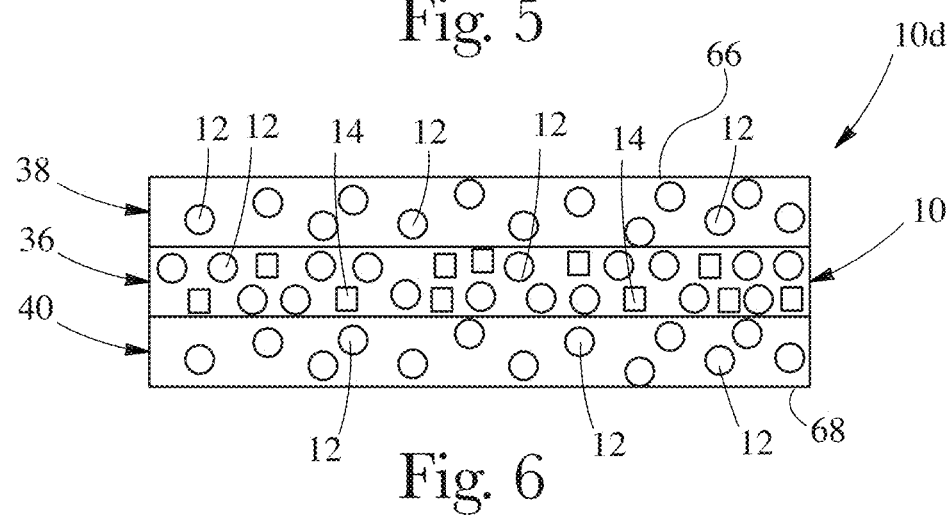
FIG. 6 is a schematic, cross-sectional representation of another example of a fibrous structure according to the present invention.

Another example of a fibrous structure of the present disclosure in accordance with the present disclosure is shown in FIG. 6. The fibrous structure 10d may comprise two or more plies, wherein one ply 36 comprises any suitable fibrous structure in accordance with the present disclosure, for example fibrous structure 10 as shown and described in FIGS. 1 and 2 and another ply 38 comprising any suitable fibrous structure, for example a fibrous structure comprising filaments 12, such as polypropylene filaments. The fibrous structure of ply 38 may be in the form of a net and/or mesh and/or other structure that comprises pores that expose one or more portions of the fibrous structure 10d to an external environment and/or at least to liquids that may come into contact, at least initially, with the fibrous structure of ply 38. In addition to ply 38, the fibrous structure 10d may further comprise ply 40. Ply 40 may comprise a fibrous structure comprising filaments 12, such as polypropylene filaments, and may be the same or different from the fibrous structure of ply 38.

Two or more of the plies 36, 38 and 40 may be bonded together, such as by thermal bonding and/or adhesive bonding, to form a multi-ply fibrous structure. After a bonding operation, especially a thermal bonding operation, it may be difficult to distinguish the plies of the fibrous structure 10d and the fibrous structure 10d may visually and/or physically be a similar to a layered fibrous structure in that one would have difficulty separating the once individual plies from each other. In one example, ply 36 may comprise a fibrous structure that exhibits a basis weight of at least about 15 $g/m^2$ and/or at least about 20 $g/m^2$ and/or at least about 25 $g/m^2$ and/or at least about 30 $g/m^2$ up to about 120 $g/m^2$ and/or 100 $g/m^2$ and/or 80 $g/m^2$ and/or 60 $g/m^2$ and the plies 38 and 42, when present, independently and individually, may comprise fibrous structures that exhibit basis weights of less than about 10 $g/m^2$ and/or less than about 7 $g/m^2$ and/or less than about 5 $g/m^2$ and/or less than about 3 $g/m^2$ and/or less than about 2 $g/m^2$ and/or to about 0 $g/m^2$ and/or 0.5 $g/m^2$.

Plies 38 and 40, when present, may help retain the solid additives, in this case the wood pulp fibers 14, on and/or within the fibrous structure of ply 36 thus reducing lint and/or dust (as compared to a single-ply fibrous structure comprising the fibrous structure of ply 36 without the plies 38 and 40) resulting from the wood pulp fibers 14 becoming free from the fibrous structure of ply 36.

The fibrous structures of the present disclosure may comprise any suitable amount of filaments and any suitable amount of solid additives. For example, the fibrous structures may comprise from about 10% to about 70% and/or from about 20% to about 60% and/or from about 30% to about 50% by dry weight of the fibrous structure of filaments and from about 90% to about 30% and/or from about 80% to about 40% and/or from about 70% to about 50% by dry weight of the fibrous structure of solid additives, such as wood pulp fibers. In one example, the fibrous structures of the present disclosure comprise filaments.

The filaments and solid additives of the present disclosure may be present in fibrous structures according to the present disclosure at weight ratios of filaments to solid additives of from at least about 1:1 and/or at least about 1:1.5 and/or at least about 1:2 and/or at least about 1:2.5 and/or at least about 1:3 and/or at least about 1:4 and/or at least about 1:5 and/or at least about 1:7 and/or at least about 1:10.

The fibrous structures of the present disclosure and/or any sanitary tissue products comprising such fibrous structures may be subjected to any post-processing operations such as embossing operations, printing operations, tuft-generating operations, thermal bonding operations, ultrasonic bonding operations, perforating operations, surface treatment operations such as application of lotions, silicones and/or other materials, folding, and mixtures thereof.

Non-limiting examples of suitable polypropylenes for making the filaments of the present disclosure are commercially available from Lyondell-Basell and Exxon-Mobil.

Any hydrophobic or non-hydrophilic materials within the fibrous structure, such as polypropylene filaments, may be surface treated and/or melt treated with a hydrophilic modifier. Non-limiting examples of surface treating hydrophilic modifiers include surfactants, such as Triton X-100. Non-limiting examples of melt treating hydrophilic modifiers that are added to the melt, such as the polypropylene melt, prior to spinning filaments, include hydrophilic modifying melt additives such as VW351 and/or S-1416 commercially available from Polyvel, Inc. and Irgasurf commercially available from Ciba. The hydrophilic modifier may be associated with the hydrophobic or non-hydrophilic material at any suitable level known in the art. In one example, the hydrophilic modifier is associated with the hydrophobic or non-hydrophilic material at a level of less than about 20% and/or less than about 15% and/or less than about 10% and/or less than about 5% and/or less than about 3% to about 0% by dry weight of the hydrophobic or non-hydrophilic material.

The fibrous structures of the present disclosure may include optional additives, each, when present, at individual levels of from about 0% and/or from about 0.01% and/or from about 0.1% and/or from about 1% and/or from about 2% to about 95% and/or to about 80% and/or to about 50% and/or to about 30% and/or to about 20% by dry weight of the fibrous structure. Non-limiting examples of optional additives include permanent wet strength agents, temporary wet strength agents, dry strength agents such as carboxymethylcellulose and/or starch, softening agents, lint reducing agents, opacity increasing agents, wetting agents, odor absorbing agents, perfumes, temperature indicating agents, color agents, dyes, osmotic materials, microbial growth detection agents, antibacterial agents and mixtures thereof. Non-limiting examples of optional melt additives include opacity increasing agents, wetting agents, odor absorbing agents, perfumes, temperature indicating agents, color agents, dyes, osmotic materials, microbial growth detection agents, antibacterial agents and mixtures thereof.

The fibrous structure of the present disclosure may itself be a sanitary tissue product. It may be convolutedly wound about a core to form a roll. It may be combined with one or more other fibrous structures as a ply to form a multi-ply sanitary tissue product. In one example, a co-formed fibrous structure of the present disclosure may be convolutedly wound about a core to form a roll of co-formed sanitary tissue product. The rolls of sanitary tissue products may also be coreless.

Liquid Composition

As discussed above, a wet wipe may include a fibrous substrate in combination with a liquid composition. The liquid composition may comprise an emollient, a clay mineral, and a rheology modifier. The liquid composition may be aqueous or emulsion-based. The liquid composition may comprise greater than about 80%, greater than about 85%, greater than about 90%, or greater than about 95% water, by weight of the liquid composition. The pH of the composition may be from about pH 3, 4, or 5 to about pH 7, 7.5, or 8. In some exemplary configurations, the pH may be from about 3.5 to about 5.5.

In addition, the liquid composition may include various optional ingredients, such as emulsifiers, film-formers, skin treatment actives, preservatives, pH buffers, anti-oxidants, metal sequestrants, particulates, polymeric opacifiers, opacifying minerals, perfumes and various other adjunct ingredients, such as described in U.S. Pat. Nos. 7,666,827; 7,005,557; 8,221,774; and U.S. Patent Application Publication No. 2011/0268777. It is to be noted that some ingredient compounds can have a multiple function and that all compounds are not necessarily present in the liquid composition.

Emollient

The liquid composition may include an emollient. Emollients may (1) hydrate the residues (for example, fecal residues or dried urine residues or menses), thus enhancing their removal from the skin, (2) hydrate and lubricate the skin, thus reducing its dryness and irritation while improving its flexibility under the wiping movement, (3) reduce the adhesive interaction between the soil and the surface, and (4) protect the skin from later irritation (for example, caused by the friction of an absorbent article or acting as a barrier from irritants present in feces or urine) as the emollient is deposited onto the skin and remains at its surface as a thin protective layer. The emollient may also improve or maintain the integrity of the skin's health as the emollient may deposit beneficial compounds such as essential fatty acids, which are present in certain vegetable oils.

Exemplary emollients for use in lotion compositions having a low pH include, but are not limited to, vegetable oils such as sunflower seed oil, canola oil, avocado oil, olive oil, emu oil, babassu oil, evening primrose oil, cottonseed oil, jojoba oil, meadowfoam seed oil, sweet almond oil, canola oil, safflower oil, coconut oil, sesame oil, rice bran oil, and grape seed oil; hydrocarbon emollients like mineral oil and petrolatum; esters like isopropyl stearate, isostearyl isononanoate, diethylhexyl fumarate, diisostearyl malate, triisocetyl citrate, stearyl stearate, methyl palmitate, and methylheptyl isostearate; petrolatum; lanolin oil and lanolin wax; long chain alcohols like cetyl alcohol, stearyl alcohol, behenyl alcohol, isostearyl alcohol, 2-hexyldecanol and myristyl alcohol; hydrophilic emollients like glycerin polyglycerols; dimethicone fluids of various molecular weights including dimethicone with a viscosity of 200 centistokes such as Momentive's ELEMENT14™ PDMS-200, or derivatized dimethicones including alkyl dimethicones such as cetyl dimethicone marketed by Dow Corning as DOW CORNING® 2502 Cosmetic Fluid, and mixtures thereof; PPG-15 stearyl ether (also known as arlatone E); vegetable butters such as shea butter, olive butter, sunflower butter, coconut butter, jojoba butter, and cocoa butter; squalane and squalene; and isoparaffins.

Emollients may include high oleic canola Oil (*Brassica campestris, B. napus, B. rapa*), very high oleic canola oil, or partially hydrogenated canola oil, pumpkin seed oil, high oleic safflower oil (*Carthamus Tinctorius*), sesame oil (*Sesamum indicum, S. oreintale*), high oleic soybean oil or partially hydrogenated soybean oil, high oleic sunflower seed oil (*Helianthus annus*) or mid oleic sunflower and mixtures thereof, olive oil, emu oil, babassu oil, evening primrose oil, palm kernel oil, cottonseed oil, jojoba oil, meadowfoam seed oil, sweet almond oil, coconut oil, rice bran oil, and grape seed oil. High oleic canola oil, palm oil, sesame oil, high oleic safflower oil, high oleic soybean oil, mid oleic sunflower seed oil, and high oleic sunflower seed oil are common plant-bred derived oils and may be also be derived from non-genetically modified organisms (non-GMO).

Non-limiting examples of emollients are commercially available from a number of vendors, including Cargill for partially hydrogenated soybean oil (i.e., Preference® 110W Soybean Oil or Preference® 300 Hi Stability Soybean Oil), mid oleic sunflower seed oil (i.e., NuSun® Mid-Oleic Sunflower Oil), high oleic sunflower seed oil (i.e., Clear Valley® High Oleic Sunflower Oil or RB Hi-Oleic Sunflower Oil), high oleic canola oil, very high oleic canola, and partially hydrogenated low erucic rapeseed oil (i.e., Clear Valley® 65 High Oleic Canola Oil and Clear Valley® 75 High Oleic Canola Oil); Lambert Technology for high oleic canola oil (i.e., Oleocal C104); Pioneer for high oleic soybean oil (i.e., Plenish®); Asoyia for low linolenic soybean oil (i.e., Ultra Low Linolenic Soybean Oil®); and Dipasa, Inc. for refined sesame oil.

Some lipophilic emollients may also act as a thickener, especially for the oil phase of an emulsion (viscosity-increasing agents, although perhaps not rheology modifiers in the sense of structuring the continuous phase of an oil-in-water emulsion composition). Such thickening emollients include, but are not limited to, hydrogenated vegetable oils like hydrogenated jojoba oil and hydrogenated jojoba wax; coconut oil; microcrystalline wax; paraffin wax; beeswax; carnauba wax; ozokerite wax; ceresine wax; myristyl alcohol; behenyl alcohol; cetyl alcohol; stearyl alcohol; cetearyl alcohol; and mixtures thereof.

In some exemplary configurations, the emollient may be liquid at 25° C., or may be solid at 25° C.

In some exemplary configurations, the liquid composition may comprise from about 0.1% % to about 5%, or about 2% to about 4%, by weight of the liquid composition, of an emollient, specifically including 0.1% increments within the above-specified range and any ranges within the specified range.

Mineral

As discussed above, the liquid composition may comprise a mineral such as a clay mineral or opacifying mineral. Surprisingly, it has been found that a liquid composition comprising an emollient and a clay mineral has little to no greasy or slimy feel. As a result, a liquid composition may comprise an emollient to deliver beneficial compounds to the skin, without having a greasy and/or slimy feel from the composition. Furthermore, a liquid composition comprising an emollient and a clay mineral has good long-term stability. In addition, a liquid composition comprising an emollient and a clay mineral and an opacifying mineral opacifies the lotion composition.

Without wishing to be bound by theory, it is believed that the clay mineral can form a hard, solid, and insoluble interfacial film on the surface of the lipophilic emollient droplets in order to inhibit the emollient drops from coalescing. In addition and as noted, it is believed that the network formed between the clay mineral and a rheology modifier like xanthan gum or certain cellulosic rheology modifiers can inhibit the Brownian motion of the lipophilic emollient droplets to further inhibit coalescence and can also aid in stabilizing suspensions comprising opacifying minerals. Brownian motion is the random movement of particles suspended in a fluid, including a liquid or a gas, resulting from their bombardment by the fast-moving atoms or molecules in the fluid. Without wishing to be bound by theory, it is believed that the negative charge contributed by the clay mineral adsorption on the surface of the lipophilic emollient droplets causes repulsion between the lipophilic emollient droplets to enhance the stability of the emulsion. Finally, without wishing to be bound by theory, it is believed that the negative and positive charges on the surface of certain clay minerals like smectite clays can lead to ionic interactions between the individual smectite clay particles. The negative charge of an individual smectite clay particle can interact with the positive charge of its neighboring smectite clay such that this ionic interaction ultimately leads to multiple smectite clay particles interacting with one another to create a structure that increases the viscosity of the aqueous composition. This aids in stabilizing the suspension which might contain mineral opacifiers like titanium dioxide or emollients like vegetable oil.

Clay minerals are also believed to have a good safety profile for use on skin of babies. The particle size of many clay minerals is about 1 micron or greater. As a result, clay minerals are not able to penetrate into the skin and cause irritation. Furthermore, clay minerals are inert and do not react to form potential irritating products. Clay minerals also improve the skin mildness of the liquid composition by binding potential irritants such that these irritants are inhibited from causing negative reactions with the skin.

Exemplary clay minerals include smectite clays such as Vanderbilt Mineral's (LLC) VEEGUM® Ultra or VEEGUM® HV or VEEGUM® HS; treated smectite clays like Brenntag's MAS-103, bentonite clays like Vanderbilt Mineral's VANATURAL® or Brenntag's ALBAGEL PURIFIED NF BC (Brenntag's BSI #4448), montmorillonite clays such as MINERAL COLLOID® BP from Southern Clay Products, Inc.; hectorite clays such as HECTABRITE® DP from Amcol Speciality Minerals; kaolinite clays such as Colloidal Kaolin USP/BC from Brenntag Specialties, Inc.; palygorskite clays such as ATTAGEL® or PHARMASORB® Colloidal from BASF Corporation; sepiolite clays such as Pangel B from Ecolog Materials Group; and saponite clays. In some exemplary configurations, the liquid composition may comprise a modified clay mineral such as modified montmorillonite clay, including CLAYTONE® AF from Southern Clay Products Inc; modified bentonite clay such as CLAYTONE® XL of Southern clay Products, Inc.; and modified hectorite clay such as BENTONE® 27V CG of Elementis Specialities. Exemplary clay minerals may include synthetic clay such as LAPONITE® clay. An exemplary LAPONITE® clay is LAPONITE® XLG from Southern Clay Products, Inc. Exemplary opacifying minerals may include titanium dioxide, composites of titanium dioxide and mica, silica coated titanium dioxides, zirconium silicate, and tin dioxide.

In order to minimize the greasy and/or slimy feel of the liquid composition, the weight ratio of emollient to clay mineral present in the liquid composition may be about 1:30 to about 30:1, or about 5:1 to about 20:1. In some exemplary configurations, the liquid composition may comprise from about 0.1% to about 1.2% %, by weight of the liquid composition, of clay mineral.

Rheology Modifier

The liquid composition may comprise one or more rheology modifiers. A rheology modifier may (1) help to stabilize the liquid composition on a fibrous structure and reduce settling of the liquid to the bottom of a package, (2) help stabilize the liquid emulsion composition by reducing the probability for phase or particle separation, (3) enhance the transfer of the liquid composition to the skin, and (4) enhance the uniformity of the layer of the liquid composition on the skin by reducing the probability of phase separation in the liquid composition. For example, rheology modifiers may help to preserve a homogeneous distribution of the liquid composition within a stack of the fibrous structures. Any composition that is in fluid form may have a tendency to migrate to the lower part of the wipes stack during prolonged storage. This effect may create an upper part of the stack of fibrous structures having less liquid composition than the bottom part of the stack.

Without wishing to be bound by theory, it is believed that rheology modifiers may enhance the liquid composition comprising an emollient and a clay mineral. The rheology modifier may minimize the greasy and/or slimy feel of a liquid composition comprising an emollient. In addition, the rheology modifier may help stabilize the suspension of particles like opacifying minerals. Without wishing to be bound by theory, it is believed that the clay mineral is wetting both the lipophilic emollient droplets and the hydrophilic aqueous phase of the liquid composition. In doing so, the clay mineral forms a barrier to prevent emollient droplets from coalescencing such that the emulsion stability is enhanced. In addition, certain clay minerals like smectites can form a platelet structure to trap individual droplets of the emollient such that the emollient is stabilized within the composition. Additionally, it is believed that the clay mineral reduces the greasy feel such that the tactile sensory characteristics of the liquid composition become more powdery and lighter in feel.

Non-limiting examples of rheology modifiers include rheology modifiers comprising: polysaccharide units, e.g. cellulose, modified celluloses, xanthan gum, diutan gum, guar gum, dextran gum, locust bean gum, carrageenan, gellan gum, konjac gum, welan gum, pectin, sclerotium gum, welan gum, starch, galactoarabinan, alginate, and modified-forms thereof; homopolymers of acrylic acid; acrylic acid cross-linked with a polyfunctional compound, e.g. carbomer and acrylate crosspolymer; copolymers of acrylic acid, acrylate esters, maleic acid and the like, generally known as the alkali swellable emulsions (ASE) group; hydrophobically-modified copolymers of acrylic acid, acrylate esters, maleic acid and the like, generally known as the hydrophobically-modified alkali swellable emulsions (HASE) group; polyethylene glycol units of varying length connected by urethane linkages and terminated with hydrophobic end groups, generally known as the hydrophobically-modified ethoxylated urethane resins (HEUR) group; organoclays; silicas; and combinations thereof.

In some exemplary configurations, the liquid composition may comprise an emollient, a clay mineral, an opacifying clay mineral, and xanthan gum.

In some exemplary configurations, the liquid composition may comprise from about 0.03% % to about 0.2%, by weight of the liquid composition, of a rheology modifier. In order to minimize the greasy and/or slimy feel of the liquid composition, the weight ratio of clay mineral to rheology modifier present in the liquid composition may be about 1:2 to about 40:1:1, or about 1:1 to about 5:1.

The weight ratio of emollient to rheology modifier present in the liquid composition may be about 1:20 to about 60:1, or about 1:2 to about 30:1.

The weight ratio of emollient to the sum of the clay mineral in combination with the rheology modifier present in the liquid composition may be about 1:15 to about 25:1, or about 1:1 to about 10:1. The peak complex viscosity of a liquid composition comprising an emollient, clay mineral, and a rheology modifier may be in the range of about 50 megapascals (mPa) to about 5000 mPa or about 200 mPA to about 100 mPA, or about 250 mPA to about 750 mPA according to the Peak Complex Viscosity Test Method provided below.

Emulsifier

The liquid composition may comprise one or more emulsifiers. The emulsifier can be an individual emulsifier or a mixture of emulsifiers. The emulsifier may be a polymeric emulsifier or a non-polymeric one. The emulsifier may be nonionic, anionic, cationic, amphoteric or zwetterionic in nature. The emulsifier may stabilize the incorporation of lipophilic emollients to the water phase of the liquid composition. The emulsifier may aid in dissolution and removal of the soils from the surface being cleansed. The emulsifier or combinations of emulsifiers may be mild, which means that the emulsifiers provide sufficient cleaning or detersive benefits but do not overly dry or otherwise harm or damage the skin.

Various emulsifiers may be used, including those selected from the group consisting of: nonionic emulsifiers, anionic emulsifiers, cationic emulsifiers, amphoteric emulsifiers, zwitterionic emulsifiers, and mixtures thereof. In some exemplary configurations, nonionic emulsifiers may be chosen, at least in part, for skin mildness properties.

In some exemplary configurations, emulsifiers may be selected from the group consisting of: monoacylglycerides and diacylglycerides, also known as monoglycerides and diglycerides, including glycerol monostearate and DIMODAN® C/B K-A, which is a monoglyceride made from cottonseed oil that is manufactured by DUPONT™ DANISCO®; propylene glycol esters of fatty acids; polyglycerol esters of fatty acids, including decaglyceryl monostearate such as POLYALDO® 10-1-S manufactured by Lonza Group Ltd.; sorbitan fatty acid esters, including sorbitan monostearate such as SPAN™ 60 manufactured by Croda International Plc., and sorbitan trioleate such as SPAN™ 85 manufactured by Croda International Plc.; polyoxyethylene derivatives of sorbitan fatty acid esters, also known as polysorbates or polyoxyethylene sorbitan esters, including polyoxyethylene 20 sorbitan monostearate such as TWEEN® 60 manufactured by Croda International Plc.; sucrose esters, including sucrose cocoate and SUCRO-SILK® HP10 manufactured by Sisterna and SISTERNA® SP70 manufactured by Sisterna; sodium and calcium stearoyl lactylate; derivatives of monoacylglycerols and diacylglycerols, including acetylated mono- and diacylglycerols, lactylated mono- and diacylglycerols, succinylated mono- and diacylglycerols, polyethylene glycol derivatives of vegetable oils like PEG-40 hydrogenated castor oil, citrate esters of mono- and diacylglycerols such as glyceryl stearate citrate sold under the designation IMWITOR® 372P(V) by Peter Cremer Incorporated, diacetyl tartaric acid esters of mono- and diacylglycerol, mono- and diacylglycerol phosphates, ethoxylated mono- and diacylglycerols; lecithins and modified lecithins; propylene glycol alginate; alkyl esters of cellulose; fatty acids, including stearic acid and oleic acid; fatty acid soaps, including sodium stearate, which is sold under the designation OP™-100V by Hallstar Incorporated; fatty alcohols, including cetyl alcohol, stearyl alcohol, and cetearyl alcohol such as TA-1618 from Procter & Gamble Chemicals; self emulsifying (SE) emulsifiers, including ARLACEL® 165 from Croda International Plc. which is a mixture of glycerol monostearate and polyoxyethylene stearate, IMWITOR® 960 K from Peter Cremer Incorporated, which is self emulsifying glyceryl stearate with a monoester content of approximately 30%, and ALDO® MSD KFG of Lonza Inc, which is also a self emulsifying glyceryl stearate; functionalized silicone emulsifiers like Abil Care 85 from Evonik Inc. and combinations thereof.

Other non-ionic emulsifiers include polyoxyethylene fatty glycerides such as polyoxyethylene 25 hydrogenated castor oil sold under the designation ARLATONE® G by Croda International Plc., polyoxyethylene 40 hydrogenated castor oil sold under the designation EMULSOGEN® hcw-049 by Clariant Inc., polyoxyethylene fatty acid esters such as polyoxyethylene 8 stearate sold under the designation MYRJ® 45 by Croda International Plc.; polyoxyethylene polyol fatty acid esters; polyoxyethylene fatty ethers, including polyoxyethylene 2 stearyl ether, polyoxyethylene 10 stearyl ether, and polyoxyethylene 20 stearyl ether all offered for sale by Croda International Plc.

Other emulsifiers include phosphate esters such as monostearyl phosphate and citrate esters such as monocetyl citrate. Alkyl glucosides are also suitable emulsifiers with examples being coco-glucoside sold under the designation PLANTACARE® 818UP by Cognis International Plc. and decyl glucoside sold under the designation PLANTAREN® 2000 N UP by Cognis International Plc. Other exemplary emulsifiers may be selected from the group consisting of: alkyl polyglucosides, polyhydroxy fatty acid amides, cocoaamphoacetate, cocoamphodiacetate, lauroamphoacetate, lauroamphodiacetate, betaines and derivatized betaines, sultaines and derivatized sultaines, and mixtures thereof.

In some exemplary configurations, the emulsifier may include sodium stearate. In some exemplary configurations, the liquid composition may comprise glycerol stearate citrate. In other exemplary configurations, the liquid composition may comprise both sodium stearate and glycerol stearate citrate.

The liquid composition may comprise a single emulsifier, or may comprise more than one emulsifier.

The emulsifier, when present in the liquid composition, may be present in an amount ranging from about 0% to about 1%, or about 0.01% to about 0.5%, or by weight of the liquid composition.

Emulsifiers that have an alkyl chain of C16 or longer having a similar structure to lipids comprising biological membranes may be particularly well suited for the liquid composition of the present disclosure.

Preservative

Controlling microbiological growth may be beneficial in water based products such as liquid compositions intended for use in wet wipes. The liquid composition may comprise a preservative or a combination of preservatives acting together as a preservative system. Preservatives and preservative systems are used interchangeably in the present disclosure to indicate one unique or a combination of preservative compounds. A preservative may be understood to be a chemical or natural compound or a combination of compounds reducing the growth of microorganisms, thus enabling a longer shelf life for a package of fibrous structures (opened or not opened) as well as creating an environment with reduced growth of microorganisms when transferred to the skin during the wiping process.

The spectrum of activity of the preservative may include bacteria, molds and yeast. Each of such microorganisms may be killed by the preservative. Another mode of action to be contemplated may be the reduction of the growth rate of the microorganisms without active killing. Both actions however result in a drastic reduction of the population of microorganisms.

Materials useful as preservatives include methylol compounds, iodopropynyl compounds, simple aromatic alcohols, paraben compounds, benzyl alcohol, benzoic acid, benzoates, sorbic acid, sorbates, phenoxyethanol, ethxylhexyglycerin, chelators such as ethylenediamine tetraacetic acid, and combinations thereof. Suitable preservative systems are described in U.S. Patent Publication No. 2005/0008680 and U.S. Patent Publication No. 2005/0008681.

Low pH buffering systems, such as a citrate-citric acid buffering system at a pH of less than about 5, may also be employed as part of the preservative system.

In some exemplary configurations, the preservative system may comprise simple aromatic alcohols (e.g., benzyl alcohol) or alkyl sorbitans like sorbitan caprylate. Materials of this type may have effective antibacterial activity. Benzyl alcohol is available from Symrise, Inc. of Teterboro, N.J. In other exemplary configurations, the preservative system may comprise a mixture of benzyl alcohol, sodium benzoate, phenoxyethanol, ethylhexylglycerin, ethylenediamine tetraacetic acid, citric acid, and sodium citrate dehydrate wherein the pH of the liquid composition is less than about 4. The total concentration of benzyl alcohol may be lower than about 0.4% by weight of the liquid composition. The total concentration of sodium benzoate may be lower than about 0.3% by weight of the liquid composition. The combination of phenoxyethanol and ethylhexylglycerin, which are available as EUXYL® PE 9010 from Schulke & Mayr GmbH of Germany, may be lower than about 0.4%. In some exemplary configurations, acidic compounds used in sufficient amount to reduce the pH of the liquid composition (e.g. pH of less than about 5) may be useful as the preservative, or as a potentiator for other preservative ingredients.

In other exemplary configurations, chelators, such as ethylenediamine tetraacetic acid and its salts, may also be used in preservative systems as a potentiator for other preservative ingredients.

Adjunct Ingredients

The liquid composition may optionally include other adjunct ingredients. Possible adjunct ingredients may be selected from a wide range of additional ingredients such as texturizers, colorants, soothing agents, anti-oxidants and medically active ingredients, such as healing actives and skin protectants. Non-limiting examples of suitable antioxidants include Vitamin E (tocopherol, including α-tocopherol, β-tocopherol, γ-tocopherol, and δ-tocopherol), tocotrienol, rosemary, oil of rosemary, ascorbic acid, sesamol, sesamolin, sesamin, catechin, citric acid, tocopherol acetate, naringenin, and mixtures thereof.

Wipe

The fibrous structure, as described above, may be utilized to form a wipe. "Wipe" may be a general term to describe a piece of material, generally non-woven material, used in cleansing hard surfaces, food, inanimate objects, toys and body parts. In particular, many currently available wipes may be intended for the cleansing of the perianal area after defecation. Other wipes may be available for the cleansing of the face or other body parts. Multiple wipes may be attached together by any suitable method to form a mitt.

The material from which a wipe is made should be strong enough to resist tearing during normal use, yet still provide softness to the user's skin, such as a child's tender skin. Additionally, the material should be at least capable of retaining its form for the duration of the user's cleansing experience.

Wipes may be generally of sufficient dimension to allow for convenient handling. Typically, the wipe may be cut and/or folded to such dimensions as part of the manufacturing process. In some instances, the wipe may be cut into individual portions so as to provide separate wipes which are often stacked and interleaved in consumer packaging. In other exemplary configurations, the wipes may be in a web form where the web has been slit and folded to a predetermined width and provided with means (e.g., perforations) to allow individual wipes to be separated from the web by a user. Suitably, an individual wipe may have a length between about 100 mm and about 250 mm and a width between about 140 mm and about 250 mm. In one exemplary configuration, the wipe may be about 200 mm long and about 180 mm wide and/or about 180 mm long and about 180 mm wide and/or about 170 mm long and about 180 mm wide and/or about 160 mm long and about 175 mm wide. The material of the wipe may generally be soft and flexible, potentially having a structured surface to enhance its cleaning performance.

It is also within the scope of the present disclosure that the wipe may be a laminate of two or more materials. Commercially available laminates, or purposely built laminates would be within the scope of the present disclosure. The laminated materials may be joined or bonded together in any suitable fashion, such as, but not limited to, ultrasonic bonding, adhesive, glue, fusion bonding, heat bonding, thermal bonding and combinations thereof. In another alternative exemplary configuration of the present disclosure the wipe may be a laminate comprising one or more layers of nonwoven materials and one or more layers of film. Examples of such optional films, include, but are not limited to, polyolefin films, such as, polyethylene film. An illustrative, but non-limiting example of a nonwoven material which is a laminate is a laminate of a 16 gsm nonwoven polypropylene and a 0.8 mm 20 gsm polyethylene film.

The wipes may also be treated to improve the softness and texture thereof by processes such as hydroentanglement or spunlacing. The wipes may be subjected to various treatments, such as, but not limited to, physical treatment, such as ring rolling, as described in U.S. Pat. No. 5,143,679; structural elongation, as described in U.S. Pat. No. 5,518,801; consolidation, as described in U.S. Pat. Nos. 5,914,084, 6,114,263, 6,129,801 and 6,383,431; stretch aperturing, as described in U.S. Pat. Nos. 5,628,097, 5,658,639 and 5,916,661; differential elongation, as described in WO Publication No. 2003/0028165A1; and other solid state formation technologies as described in U.S. Publication No. 2004/0131820A1 and U.S. Publication No. 2004/0265534A1 and zone activation and the like; chemical treatment, such as, but not limited to, rendering part or all of the fibrous structure hydrophobic, and/or hydrophilic, and the like; thermal treatment, such as, but not limited to, softening of fibers by heating, thermal bonding and the like; and combinations thereof.

The wipe may have a basis weight of at least about 30 grams/m$^2$ and/or at least about 35 grams/m$^2$ and/or at least about 40 grams/m$^2$. In one example, the wipe may have a basis weight of at least about 45 grams/m$^2$. In another example, the wipe basis weight may be less than about 100 grams/m$^2$. In another example, wipes may have a basis weight between about 45 grams/m$^2$ and about 75 grams/m$^2$, and in yet another exemplary configuration a basis weight between about 45 grams/m$^2$ and about 65 grams/m$^2$.

In one example of the present disclosure the surface of wipe may be essentially flat. In another example of the present disclosure the surface of the wipe may optionally contain raised and/or lowered portions. These can be in the form of logos, indicia, trademarks, geometric patterns, images of the surfaces that the fibrous structure is intended to clean (i.e., infant's body, face, etc.). They may be randomly arranged on the surface of the wipe or be in a repetitive pattern of some form.

In another example of the present disclosure the wipe may be biodegradable. For example the wipe could be made from a biodegradable material such as a polyesteramide, or high wet strength cellulose.

In one example of the present disclosure, the fibrous structure is combined with a liquid composition to form a wet wipe, such as a baby wipe. A plurality of the wet wipes may be stacked one on top of the other and may be contained in a container, such as a plastic tub or a film wrapper. In one example, the stack of wet wipes (typically about 40 to 80 wipes/stack) may exhibit a height of from about 50 to about 300 mm and/or from about 75 to about 125 mm. The wet wipes may comprise a liquid composition. The wet wipes may be stored long term in a stack in a liquid impervious container or film pouch without all of the lotion draining from the top of the stack to the bottom of the stack.

In another example, the wet wipes may exhibit a saturation loading (g liquid composition to g of dry wipe) of from about 1.5 to about 6.0 g/g. The liquid composition may exhibit a surface tension of from about 20 to about 35 and/or from about 28 to about 32 dynes/cm.

In one example, the wet wipes are present in a stack of wet wipes that exhibits a height of from about 50 to about 300 mm and/or from about 75 to about 200 mm and/or from about 75 to about 125 mm, wherein the stack of wet wipes exhibits a saturation gradient index of from about 1.0 to about 2.0 and/or from about 1.0 to about 1.7 and/or from about 1.0 to about 1.5.

The fibrous structures or wipes of the present disclosure may be saturation loaded with a liquid composition to form a wet fibrous structure or wipe. The loading may occur individually, or after the fibrous structures or wipes are place in a stack, such as within a liquid impervious container or packet. In one example, the wet wipes may be saturation loaded with from about 1.5 g to about 6.0 g and/or from about 2.5 g to about 4.0 g of liquid composition per g of wipe.

The fibrous structures or wipes of the present disclosure may be placed in the interior of a container, which may be liquid impervious, such as a plastic tub or a sealable packet, for storage and eventual sale to the consumer. The wipes may be folded and stacked. The wipes of the present disclosure may be folded in any of various known folding patterns, such as C-folding, Z-folding and quarter-folding. Use of a Z-fold pattern may enable a folded stack of wipes to be interleaved with overlapping portions. Alternatively, the wipes may include a continuous strip of material which has perforations between each wipe and which may be arranged in a stack or wound into a roll for dispensing, one after the other, from a container, which may be liquid impervious.

The fibrous structures or wipes of the present disclosure may further comprise prints, which may provide aesthetic appeal. Non-limiting examples of prints include figures, patterns, letters, pictures and combinations thereof.

Exemplary fibrous structures are described in U.S. Patent Application Publication No. 2011/0244199.

The fibrous structure of the present disclosure may have a Liquid Absorptive Capacity of greater than 11 g/g and/or greater than 12 g/g and/or greater than 13 g/g and/or greater than 14 g/g and/or greater than 15 g/g as measured according to the Liquid Absorptive Capacity Test Method described herein.

The wet wipes of the present disclosure may exhibit a Liquid Absorptive Capacity of at least 2.5 g/g and/or at least 4.0 g/g and/or at least 7 g/g and/or at least 12 g/g and/or at least 13 g/g and/or at least 13.5 g/g and/or to about 30.0 g/g and/or to about 20 g/g and/or to about 15.0 g/g as measured according to the Liquid Absorptive Capacity Test Method described herein.

The wet wipes of the present disclosure may have a caliper of greater than about 0.1 millimeters (mm) measured according to the Caliper Test Method described herein.

The wet wipes of the present disclosure may have a Tactile Sensory Coefficient of Friction of less than 0.60, or less than 0.58, or less than 0.56, or less than 0.54, or less than 0.52, or less than 0.50, or less than 0.48, or less than 0.46, or less than 0.44, or less than 0.42, or less than 0.40, measured according to the Tactile Sensory Coefficient of Friction Test Method described herein.

The wet wipes of the present disclosure may have a Cleaning Coefficient of Friction of greater than 0.40, or greater than 0.50, or greater than 0.60, or greater than 0.70, or greater than 0.80, measured according to the Cleaning Coefficient of Friction Test Method described herein.

The wet wipes of the present disclosure may have a Wet to Dry Drape Ratio of less than about 0.80, or less than about 0.75, or less than about 0.7, or less than about 0.65, or less than about 0.60, or less than about 0.55, or less than about 0.50, or less than about 0.45, or less than about 0.40, measured according to the Wet to Dry Drape Ratio Test Method described herein.

The wet wipes of the present disclosure may have a Compressive Modulus of greater than about 4.75 [log(gsi)], or greater than about 4.80 [log(gsi)], or greater than about 4.85 [log(gsi)], or greater than about 4.90 [log(gsi)], or greater than about 4.95 [log(gsi)], or greater than about 5.00 [log(gsi)], or greater than about 5.05 [log(gsi)], or greater than about 5.10 [log(gsi)], or greater than about 5.15 [log (gsi)], measured according to the Compressive Modulus Test Method described herein.

Stacks of wet wipes of the present disclosure may have a SGI from about 1.0 to about 1.5, or from about 1.0 to about 1.4, or about 1.0 to about 1.3, or about 1.0 to about 1.2, or about 1.0 to about 1.1.

Method for Making a Fibrous Structure

Figure 7:
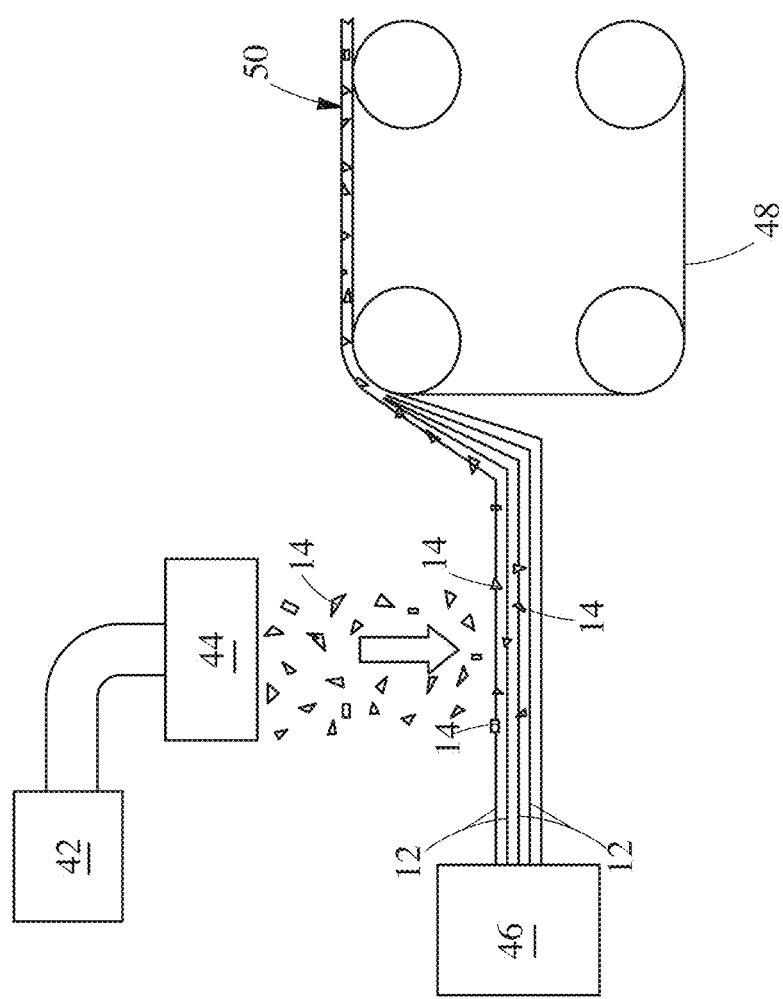
FIG. 7 is a schematic representation of an example of a process for making a fibrous structure according to the present disclosure.
Figure 8:
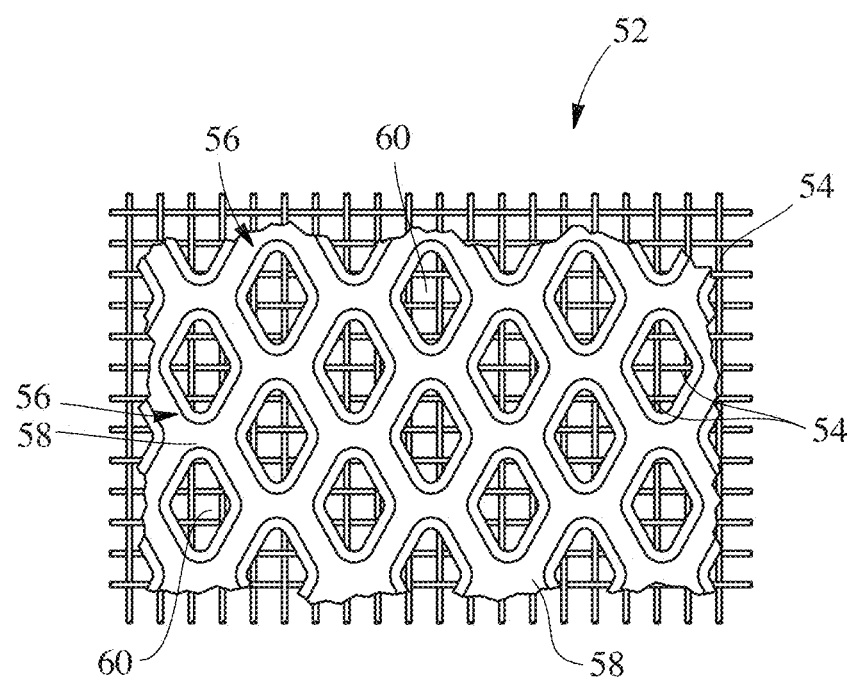
FIG. 8 is a schematic representation of an example of a patterned belt for use in a process according to the present disclosure.

A non-limiting example of a method for making a fibrous structure according to the present invention is represented in FIG. 7. The method shown in FIG. 7 comprises the step of mixing a plurality of solid additives 14 with a plurality of filaments 12. In one example, the solid additives 14 are wood pulp fibers, such as SSK fibers and/or Eucalyptus fibers, and the filaments 12 are polypropylene filaments. The solid additives 14 may be combined with the filaments 12, such as by being delivered to a stream of filaments 12 from a hammermill 42 via a solid additive spreader 44 to form a mixture of filaments 12 and solid additives 14. The filaments 12 may be created by meltblowing from a meltblow die 46. The mixture of solid additives 14 and filaments 12 are collected on a collection device, such as a belt 48 to form a fibrous structure 50. The collection device may be a patterned and/or molded belt that results in the fibrous structure exhibiting a surface pattern, such as a non-random, repeating pattern of microregions. The molded belt may have a three-dimensional pattern on it that gets imparted to the fibrous structure 50 during the process. For example, the patterned belt 52, as shown in FIG. 8, may comprise a reinforcing structure, such as a fabric 54, upon which a polymer resin 56 is applied in a pattern. The pattern may comprise a continuous or semi-continuous network 58 of the polymer resin 56 within which one or more discrete conduits 60 are arranged.

In one example of the present invention, the fibrous structures are made using a die comprising at least one filament-forming hole, and/or 2 or more and/or 3 or more rows of filament-forming holes from which filaments are spun. At least one row of holes contains 2 or more and/or 3 or more and/or 10 or more filament-forming holes. In addition to the filament-forming holes, the die comprises fluid-releasing holes, such as gas-releasing holes, in one example air-releasing holes, that provide attenuation to the filaments formed from the filament-forming holes. One or more fluid-releasing holes may be associated with a filament-forming hole such that the fluid exiting the fluid-releasing hole is parallel or substantially parallel (rather than angled like a knife-edge die) to an exterior surface of a filament exiting the filament-forming hole. In one example, the fluid exiting the fluid-releasing hole contacts the exterior surface of a filament formed from a filament-forming hole at an angle of less than 30° and/or less than 20° and/or less than 10° and/or less than 5° and/or about 0°. One or more fluid releasing holes may be arranged around a filament-forming hole. In one example, one or more fluid-releasing holes are associated with a single filament-forming hole such that the fluid exiting the one or more fluid releasing holes contacts the exterior surface of a single filament formed from the single filament-forming hole. In one example, the fluid-releasing hole permits a fluid, such as a gas, for example air, to contact the exterior surface of a filament formed from a filament-forming hole rather than contacting an inner surface of a filament, such as what happens when a hollow filament is formed.

Figure 9:
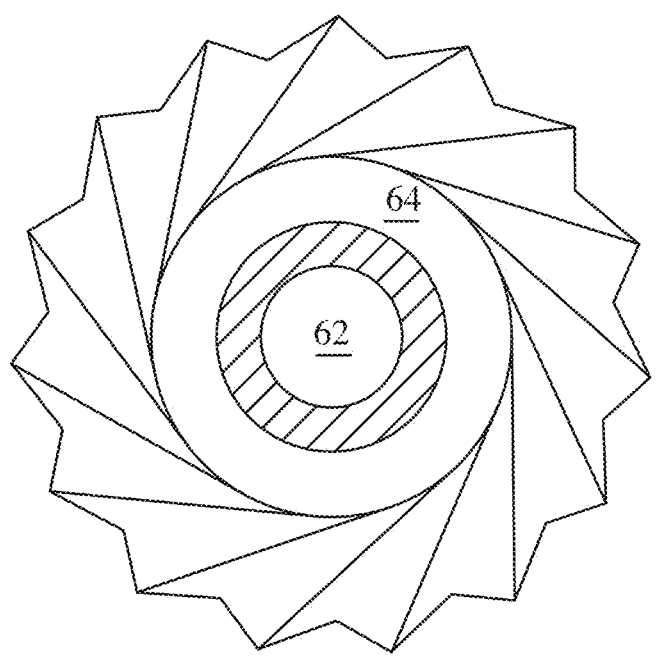
FIG. 9 is a schematic representation of an example of a filament-forming hole and fluid-releasing hole from a suitable die useful in making a fibrous structure according to the present disclosure.

In one example, the die comprises a filament-forming hole positioned within a fluid-releasing hole. The fluid-releasing hole 64 may be concentrically or substantially concentrically positioned around a filament-forming hole 62 such as is shown in FIG. 9.

After the fibrous structure 50 has been formed on the collection device, such as a patterned belt or a woven fabric for example a through-air-drying fabric, the fibrous structure 50 may be calendered, for example, while the fibrous structure is still on the collection device. In addition, the fibrous structure 50 may be subjected to post-processing operations such as embossing, thermal bonding, tuft-generating operations, moisture-imparting operations, and surface treating operations to form a finished fibrous structure. One example of a surface treating operation that the fibrous structure may be subjected to is the surface application of an elastomeric binder, such as ethylene vinyl acetate (EVA), latexes, and other elastomeric binders. Such an elastomeric binder may aid in reducing the lint created from the fibrous structure during use by consumers. The elastomeric binder may be applied to one or more surfaces of the fibrous structure in a pattern, especially a non-random, repeating pattern of microregions, or in a manner that covers or substantially covers the entire surface(s) of the fibrous structure.

In one example, the fibrous structure 50 and/or the finished fibrous structure may be combined with one or more other fibrous structures. For example, another fibrous structure, such as a filament-containing fibrous structure, such as a polypropylene filament fibrous structure may be associated with a surface of the fibrous structure 50 and/or the finished fibrous structure. The polypropylene filament fibrous structure may be formed by meltblowing polypropylene filaments (filaments that comprise a second polymer that may be the same or different from the polymer of the filaments in the fibrous structure 50) onto a surface of the fibrous structure 50 and/or finished fibrous structure. In another example, the polypropylene filament fibrous structure may be formed by meltblowing filaments comprising a second polymer that may be the same or different from the polymer of the filaments in the fibrous structure 50 onto a collection device to form the polypropylene filament fibrous structure. The polypropylene filament fibrous structure may then be combined with the fibrous structure 50 or the finished fibrous structure to make a two-ply fibrous structure—three-ply if the fibrous structure 50 or the finished fibrous structure is positioned between two plies of the polypropylene filament fibrous structure like that shown in FIG. 6 for example. The polypropylene filament fibrous structure may be thermally bonded to the fibrous structure 50 or the finished fibrous structure via a thermal bonding operation.

In yet another example, the fibrous structure 50 and/or finished fibrous structure may be combined with a filament-containing fibrous structure such that the filament-containing fibrous structure, such as a polysaccharide filament fibrous structure, such as a starch filament fibrous structure, is positioned between two fibrous structures 50 or two finished fibrous structures like that shown in FIG. 6 for example.

In one example of the present invention, the method for making a fibrous structure according to the present invention comprises the step of combining a plurality of filaments and optionally, a plurality of solid additives to form a fibrous structure that exhibits the properties of the fibrous structures of the present invention described herein. In one example, the filaments comprise thermoplastic filaments. In one example, the filaments comprise polypropylene filaments. In still another example, the filaments comprise natural polymer filaments. The method may further comprise subjecting the fibrous structure to one or more processing operations, such as calendaring the fibrous structure. In yet another example, the method further comprises the step of depositing the filaments onto a patterned belt that creates a non-random, repeating pattern of micro regions.

In still another example, two plies of fibrous structure 50 comprising a non-random, repeating pattern of microregions may be associated with one another such that protruding microregions, such as pillows, face inward into the two-ply fibrous structure formed.

The process for making fibrous structure 50 may be close coupled (where the fibrous structure is convolutedly wound into a roll prior to proceeding to a converting operation) or directly coupled (where the fibrous structure is not convolutedly wound into a roll prior to proceeding to a converting operation) with a converting operation to emboss, print, deform, surface treat, thermal bond, cut, stack or other post-forming operation known to those in the art. For purposes of the present invention, direct coupling means that the fibrous structure 50 can proceed directly into a converting operation rather than, for example, being convolutedly wound into a roll and then unwound to proceed through a converting operation.

In one example, the fibrous structure is embossed, cut into sheets, and collected in stacks of fibrous structures.

The process of the present invention may include preparing individual rolls and/or sheets and/or stacks of sheets of fibrous structure and/or sanitary tissue product comprising such fibrous structure(s) that are suitable for consumer use.

Non-Limiting Examples of Processes for Making a Fibrous Structure of the Present Invention Process Example 1

A 21%:27.5%:47.5%:4% blend of Lyondell-Basell PH835 polypropylene:Lyondell-Basell Metocene MF650W polypropylene:Lyondell-Basell Metocene MF650X polypropylene:Ampacet 412951 Opacifying agent is dry blended, to form a melt blend. The melt blend is heated to 400° F. through a melt extruder. A 15.5 inch wide Biax 12 row spinnerette with 192 nozzles per cross-direction inch, commercially available from Biax Fiberfilm Corporation, is utilized. 40 nozzles per cross-direction inch of the 192 nozzles have a 0.018 inch inside diameter while the remaining nozzles are solid, i.e., there is no opening in the nozzle. Approximately 0.19 grams per hole per minute (ghm) of the melt blend is extruded from the open nozzles to form meltblown filaments from the melt blend. Approximately 415 SCFM of compressed air is heated such that the air exhibits a temperature of 395° F. at the spinnerette. Approximately 600 g/minute of Golden Isle (from Georgia Pacific) 4825 semi-treated SSK pulp is defibrillated through a hammermill to form wood pulp fibers (solid additive). Air at 85-90° F. and 85% relative humidity (RH) is drawn into the hammermill. Approximately 2400 SCFM of air carries the pulp fibers to two solid additive spreaders. The solid additive spreaders turn the pulp fibers and distribute the pulp fibers in the cross-direction such that the pulp fibers are injected into the meltblown filaments through a 4 inch×15 inch cross-direction (CD) slot. The two solid additive spreaders are on opposite sides of the meltblown filaments facing one another. A forming box surrounds the area where the meltblown filaments and pulp fibers are commingled. This forming box is designed to reduce the amount of air allowed to enter or escape from this commingling area. A forming vacuum pulls air through a collection device, such as a patterned belt, thus collecting the commingled meltblown filaments and pulp fibers to form a fibrous structure. The fibrous structure formed by this process comprises about 75% by dry fibrous structure weight of pulp and about 25% by dry fibrous structure weight of meltblown filaments.

Optionally, a meltblown layer of the meltblown filaments, such as a scrim, can be added to one or both sides of the above formed fibrous structure. This addition of the meltblown layer can help reduce the lint created from the fibrous structure during use by consumers and is preferably performed prior to any thermal bonding operation of the fibrous structure. The meltblown filaments for the exterior layers can be the same or different than the meltblown filaments used on the opposite layer or in the center layer(s).

The fibrous structure may be convolutedly wound to form a roll of fibrous structure. The end edges of the roll of fibrous structure may be contacted with a material to create bond regions.

Process Example 2

A 20%:27.5%:47.5%:5% blend of Lyondell-Basell PH835 polypropylene:Lyondell-Basell Metocene MF650W polypropylene:Exxon-Mobil PP3546 polypropylene:Polyvel S-1416 wetting agent is dry blended, to form a melt blend. The melt blend is heated to 475° F. through a melt extruder. A 15.5 inch wide Biax 12 row spinnerette with 192 nozzles per cross-direction inch, commercially available from Biax Fiberfilm Corporation, is utilized. 40 nozzles per cross-direction inch of the 192 nozzles have a 0.018 inch inside diameter while the remaining nozzles are solid, i.e. there is no opening in the nozzle. Approximately 0.19 grams per hole per minute (ghm) of the melt blend is extruded from the open nozzles to form meltblown filaments from the melt blend. Approximately 375 SCFM of compressed air is heated such that the air exhibits a temperature of about 395° F. at the spinnerette. Approximately 475 g/minute of Golden Isle (from Georgia Pacific) 4825 semi-treated SSK pulp is defibrillated through a hammermill to form SSK wood pulp fibers (solid additive). Air at a temperature of about 85 to 90° F. and about 85% relative humidity (RH) is drawn into the hammermill. Approximately 1200 SCFM of air carries the pulp fibers to a solid additive spreader. The solid additive spreader turns the pulp fibers and distributes the pulp fibers in the cross-direction such that the pulp fibers are injected into the meltblown filaments in a perpendicular fashion (with respect to the flow of the meltblown filaments) through a 4 inch×15 inch cross-direction (CD) slot. A forming box surrounds the area where the meltblown filaments and pulp fibers are commingled. This forming box is designed to reduce the amount of air allowed to enter or escape from this commingling area; however, there is an additional 4 inch×15 inch spreader opposite the solid additive spreader designed to add cooling air. Approximately 1000 SCFM of air at approximately 80° F. is added through this additional spreader. A forming vacuum pulls air through a collection device, such as a patterned belt, thus collecting the commingled meltblown filaments and pulp fibers to form a fibrous structure comprising a pattern of non-random, repeating microregions. The fibrous structure formed by this process comprises about 75% by dry fibrous structure weight of pulp and about 25% by dry fibrous structure weight of meltblown filaments.

Optionally, a meltblown layer of the meltblown filaments, such as a scrim, can be added to one or both sides of the above formed fibrous structure. This addition of the meltblown layer can help reduce the lint created from the fibrous structure during use by consumers and is preferably performed prior to any thermal bonding operation of the fibrous structure. The meltblown filaments for the exterior layers can be the same or different than the meltblown filaments used on the opposite layer or in the center layer(s).

The fibrous structure may be convolutedly wound to form a roll of fibrous structure. The end edges of the roll of fibrous structure may be contacted with a material to create bond regions.

Non-Limiting Examples of Fibrous Structures

Fibrous Structure Example 1

Figure 10:
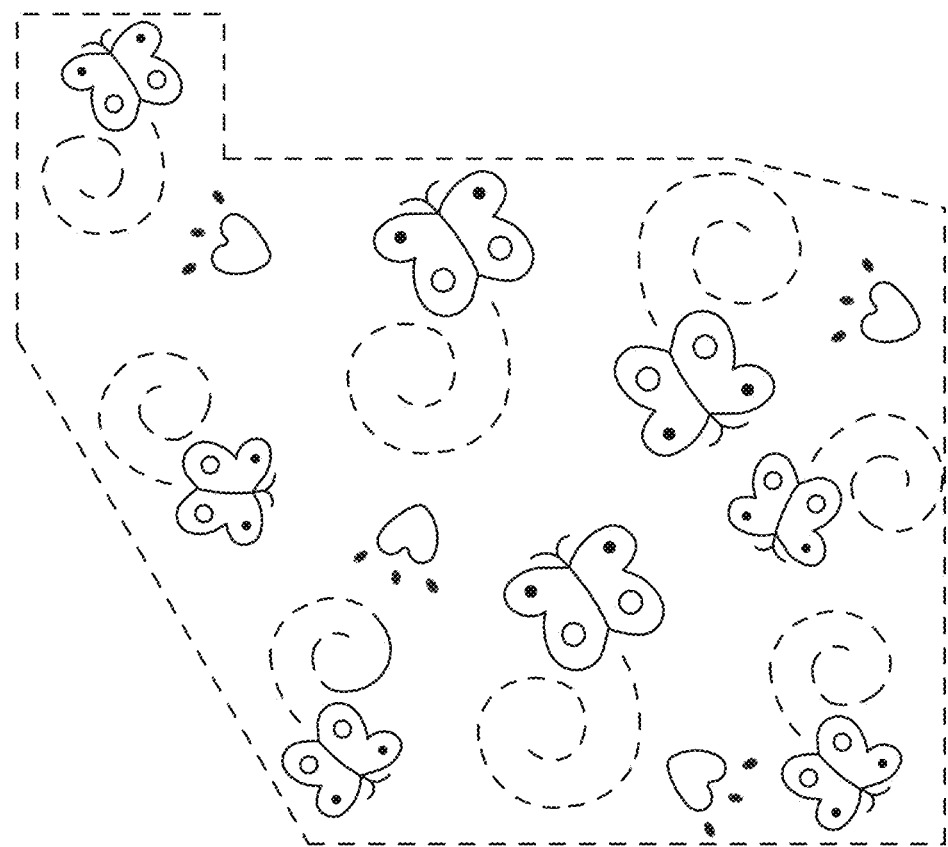
FIG. 10 is an example of a pattern that can be imparted to a fibrous structure of the present disclosure.
Figure 11:
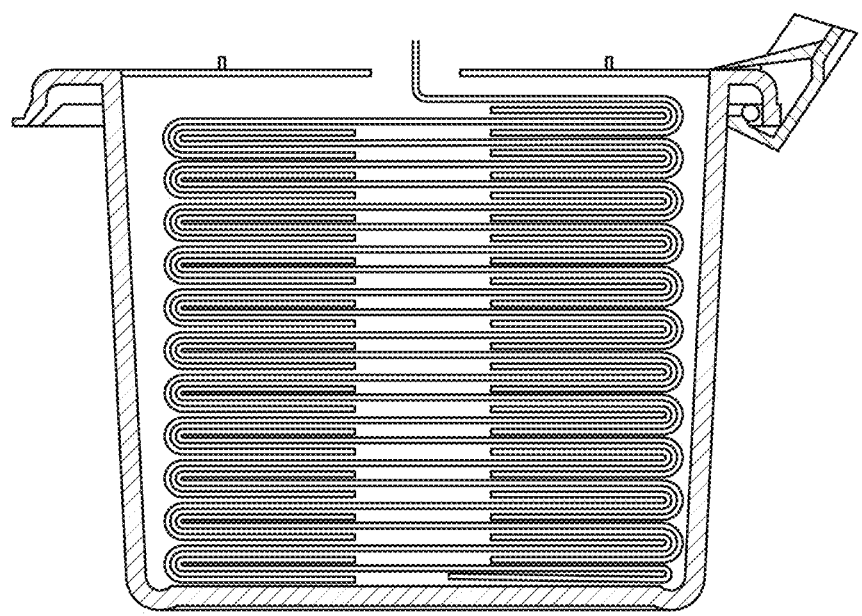
FIG. 11 is a schematic representation of an example of a stack of fibrous structures in a tub.

A pre-moistened wipe according to the present invention is prepared as follows. A fibrous structure of the present invention of about 51 g/m² that comprises a thermal bonded pattern as shown in FIG. 10 is saturation loaded with a liquid composition according to the present invention to an average saturation loading of about 350% of the basis weight of the wipe. The wipes are then Z-folded and placed in a stack to a height of about 57 mm as shown in FIG. 11.

Fibrous Structure Example 2

A pre-moistened wipe according to the present invention is prepared as follows. A fibrous structure of the present invention of about 56 g/m² that comprises a thermal bonded pattern as shown in FIG. 10 is saturation loaded with a liquid composition according to the present invention to an average saturation loading of about 350% of the basis weight of the wipe. The wipes are then Z-folded and placed in a stack to a height of about 63 mm as shown in FIG. 11.

Table 1 shows Liquid Composition Example 1, which is an illustrative, non-limiting formula for a cleansing composition of the present disclosure comprising an emollient and a clay mineral.

TABLE 1

| Liquid Composition Example 1 | |
| --- | --- |
| Ingredient Name | Weight % |
| Water | Q.S. |
| Disodium EDTA | 0.10 |
| Sodium Benzoate | 0.12 |
| Trisodium Citrate | 0.30 |
| Xanthan Gum | 0.11 |
| Montmorillonite Clay† | 0.33 |
| Sodium Stearate | 0.20 |
| Glyceryl Stearate Citrate△ | 0.38 |
| Phenoxyethanol Ethylhexylglycerine° | 0.30 |

TABLE 1-continued

| Liquid Composition Example 1 | |
| --- | --- |
| Ingredient Name | Weight % |
| Benzyl Alcohol | 0.30 |
| Sunflower Seed Oil⁰ | 2.80 |
| Citric Acid | 0.59 |
| Total | 100 |

†Mineral Colloid BP from Southern Clay Products of Austin, TX

OP-100V from Hallstar Company of Chicago, IL

△Imwitor 372 from Peter Cremer of Cincinnati, OH

°EUXYL ® PE 9010, available from Schulke & Mayr GmbH of Germany

⁰High Oleic Sunflower Seed Oil, available from Cargill of Minneapolis, MN

Table 2 shows Liquid Composition Example 2, which is an illustrative, non-limiting formula for a liquid composition of the present disclosure.

TABLE 2

| Liquid Composition Example 2 | |
| --- | --- |
| Ingredient Name | Weight % |
| Water | Q.S. |
| Disodium EDTA | 0.10 |
| Sodium Benzoate | 0.12 |
| Trisodium Citrate | 0.31 |
| Xanthan Gum | 0.09 |
| Veegum Ultra | 0.90 |
| Titanium Dioxide△ | 0.15 |
| Phenoxyethanol Ethylhexylglycerine° | 0.300 |
| Benzyl Alcohol | 0.300 |
| Citric Acid | 0.51 |
| Total | 100 |

Veegum Ultra available from Vanderbilt Minerals LLC, Norwalk, CT

△Titanium Dioxide available from Brenntag North America Inc in Reading, PA

°EUXYL ® PE 9010, available from Schulke & Mayr GmbH of Germany

Figure 12:
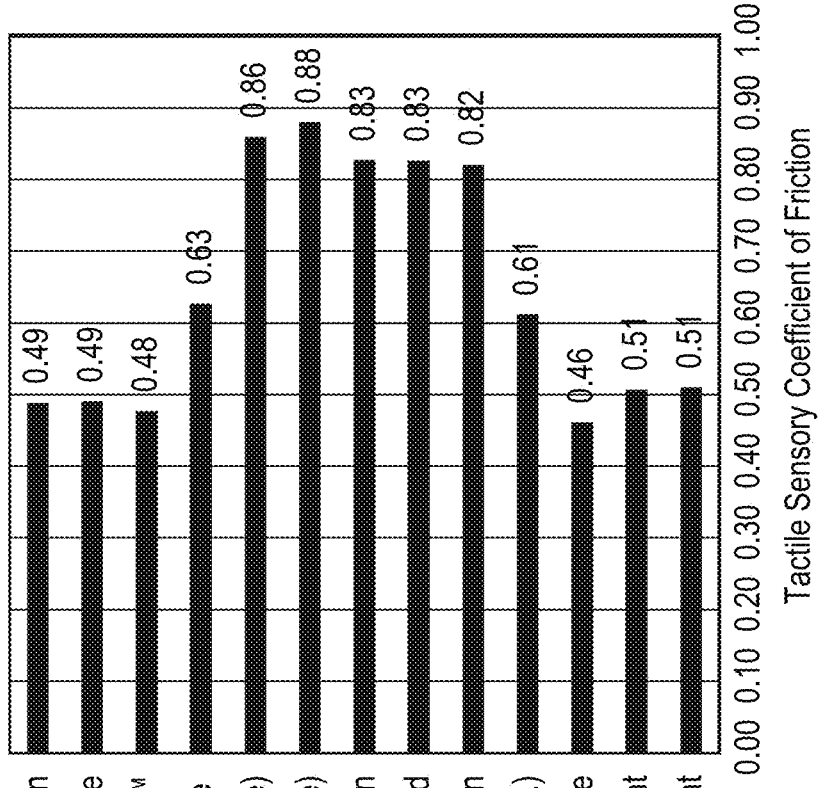
FIG. 12 is a plot of the Tactile Sensation Coefficient of Friction of known or commercially available wet wipes and exemplary wet wipes of the present disclosure.
Figure 13:
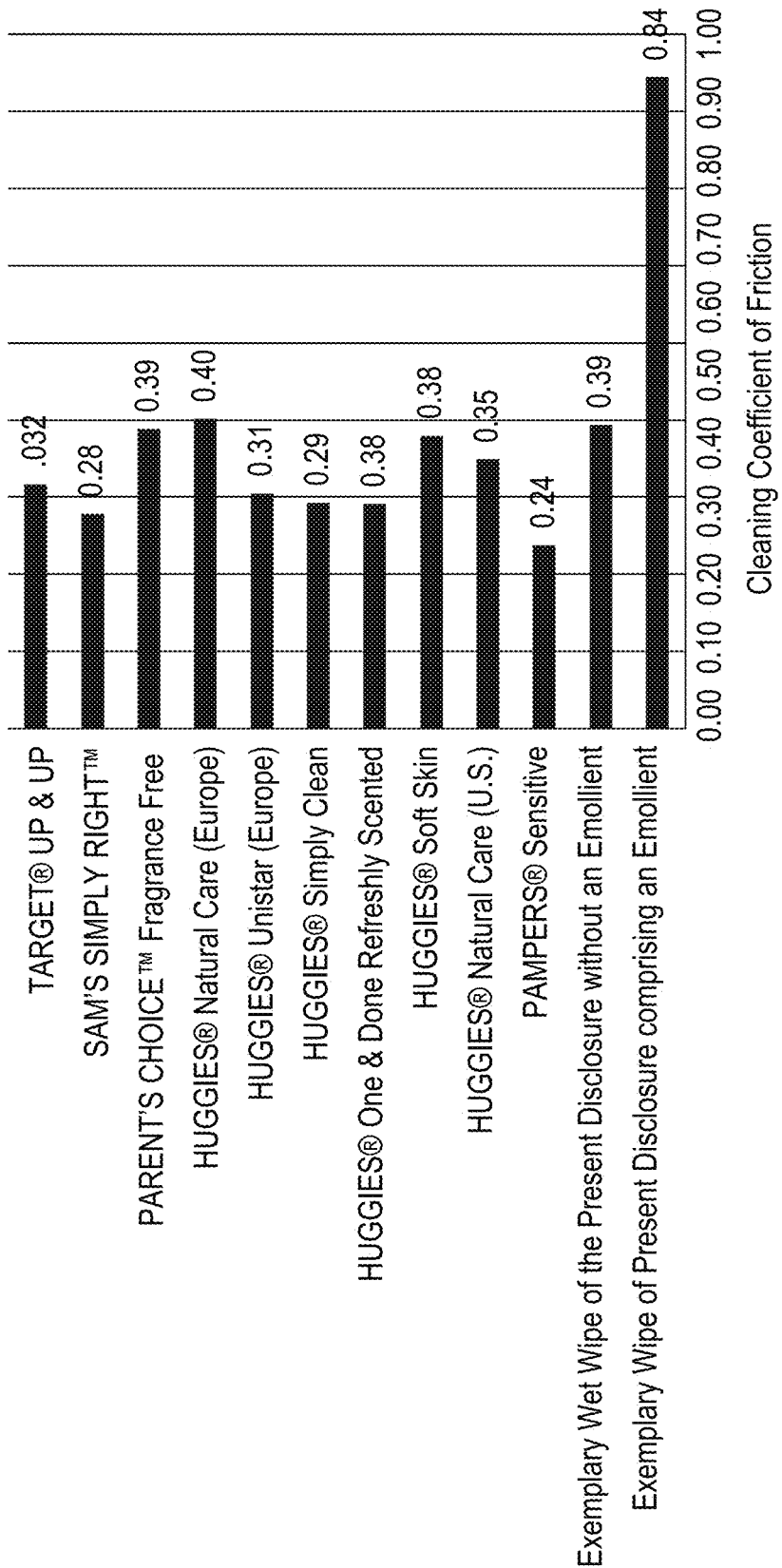
FIG. 13 is a plot of the Cleaning Coefficient of Friction of known or commercially available wet wipes and exemplary wet wipes of the present disclosure.
Figure 14:
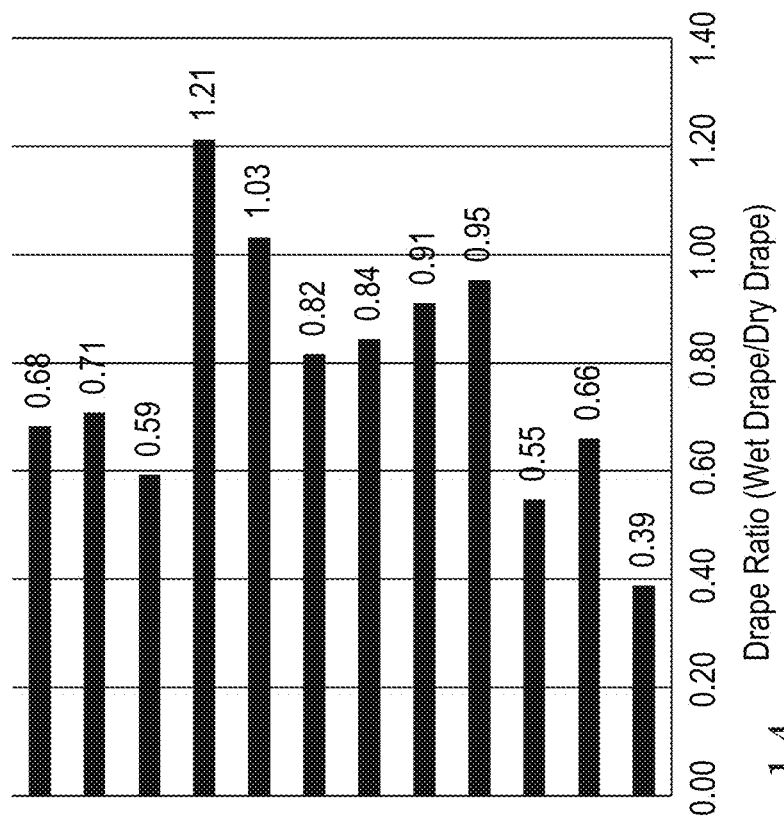
FIG. 14 is a plot of the Wet to Dry Drape Ratio of known or commercially available wet wipes and exemplary wet wipes of the present disclosure.
Figure 15:
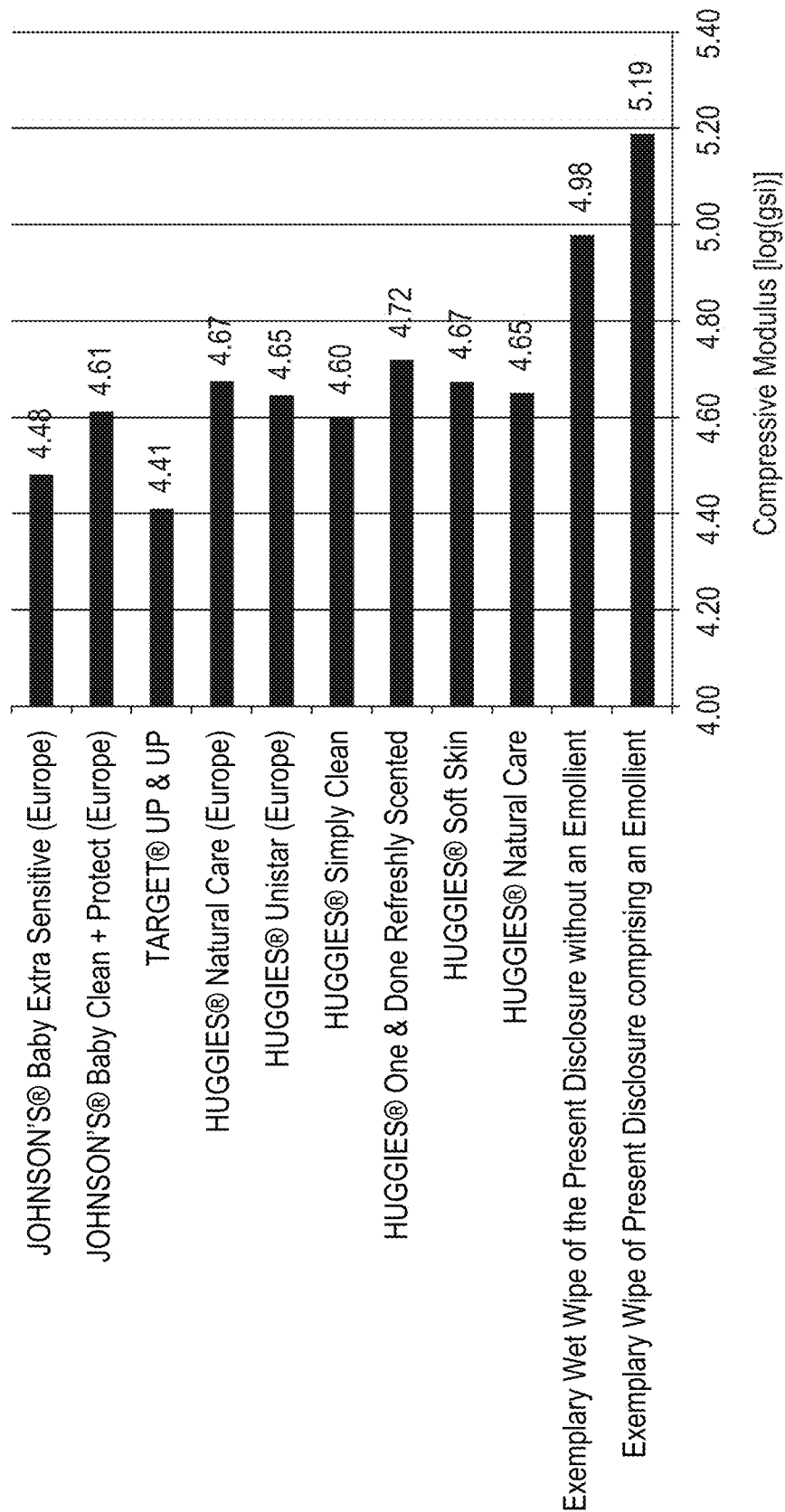
FIG. 15 is a plot of the Compressive Modulus of known or commercially available wet wipes and exemplary wet wipes of the present disclosure.

To further illustrate the wet wipes of the present disclosure, Tables 3-6 shown below set forth properties of known and/or commercially available wet wipes and two exemplary wet wipes of the present disclosure. FIG. 12 is a plot of the Tactile Sensation Coefficient of Friction of known or commercially available wet wipes and two exemplary wet wipes of the present disclosure. FIG. 13 is a plot of the Cleaning Coefficient of Friction of known or commercially available wet wipes and two exemplary wet wipes of the present disclosure. As shown in Table 3 and FIG. 13, the Cleaning Coefficient of Friction on a first side of the wet wipe and the Cleaning Coefficient of Friction on a second, opposing side of the wet wipe may be different. FIG. 14 is a plot of the Wet to Dry Drape Ratio of known or commercially available wet wipes and two exemplary wet wipes of the present disclosure. FIG. 15 is a plot of the Compressive Modulus of known or commercially available wet wipes and two exemplary wet wipes of the present disclosure.

TABLE 3

| | Contains Filaments | Contains Pulp Fibers | Contains Synthetic Fibers | Basis Weight (gsm) | Tactile Sensory Coefficient of Friction (CoF) | Cleaning Coefficient of Friction (CoF) | Difference in Cleaning CoF between first and second sides of wipe |
|---|---|---|---|---|---|---|---|
| Exemplary Wipe of Present Disclosure comprising an Emollient | yes | yes | yes | 52 | 0.51 | 0.84 | 0.35 |
| Exemplary Wet Wipe of the Present Disclosure without an Emollient | yes | yes | yes | 52 | 0.51 | 0.39 | 0.16 |
| PAMPERS ® Sensitive | no | no | yes | 50 | 0.46 | 0.24 | 0.01 |
| HUGGIES ® Natural Care (U.S.) | yes | yes | yes | 60 | 0.61 | 0.35 | 0.00 |
| HUGGIES ® Soft Skin | yes | yes | yes | 67 | 0.82 | 0.38 | 0.03 |
| HUGGIES ® One & Done Refreshly Scented | yes | yes | yes | 66 | 0.83 | 0.29 | 0.03 |
| HUGGIES ® Simply Clean | yes | yes | yes | 50 | 0.83 | 0.29 | 0.02 |
| PARENT'S CHOICE ™ Fragrance Free | no | yes | yes | 58 | 0.63 | 0.39 | 0.01 |
| SAM'S SIMPLY RIGHT ™ | — | no | yes | 52 | 0.48 | 0.28 | 0.00 |
| Walgreen's WELL BEGINNINGS ™ Sensitive | — | no | yes | 52 | 0.49 | — | — |
| Walgreen's BABYGANICS ™ Thick Kleen | no | — | yes | 57 | 0.49 | — | — |
| HUGGIES ® Unistar (Europe) | yes | yes | yes | 39 | 0.88 | 0.31 | 0.01 |
| HUGGIES ® Natural Care (Europe) | yes | yes | yes | 49 | 0.86 | 0.40 | 0.00 |
| TARGET ® UP & UP ® | no | no | yes | 51 | — | 0.32 | 0.03 |

TABLE 4

| | Contains Filaments | Contains Pulp Fibers | Contains Synthetic Fibers | Wet Drape (N) | Dry Drape (N) | Drape Ratio (Wet Drape/Dry Drape) | Caliper (mm) | Compressive Modulus [log(gsi)] |
|---|---|---|---|---|---|---|---|---|
| Exemplary Wipe of Present Disclosure comprising an Emollient | yes | yes | yes | 0.54 | 1.39 | 0.39 | 0.57 | 5.19 |
| Exemplary Wet Wipe of the Present Disclosure without an Emollient | yes | yes | yes | 0.71 | 1.18 | 0.66 | 0.53 | 4.98 |
| PAMPERS ® Sensitive | no | no | yes | 0.45 | 0.83 | 0.55 | 0.57 | — |
| HUGGIES ® Natural Care (U.S.) | yes | yes | yes | 0.80 | 0.83 | 0.95 | 0.75 | 4.65 |
| HUGGIES ® Soft Skin | yes | yes | yes | 0.77 | 0.85 | 0.91 | 0.69 | 4.67 |
| HUGGIES ® One & Done Refreshly Scented | yes | yes | yes | 0.87 | 1.05 | 0.84 | 0.75 | 4.72 |
| HUGGIES ® Simply Clean | yes | yes | yes | 0.59 | 0.74 | 0.82 | 0.62 | 4.60 |
| PARENT'S CHOICE ™ Fragrance Free | no | yes | yes | 0.84 | 1.42 | 0.59 | 0.53 | — |
| SAM'S SIMPLY RIGHT ™ | — | no | yes | 0.45 | 0.64 | 0.71 | 0.70 | — |
| HUGGIES ® Unistar (Europe) | yes | yes | yes | 0.58 | 0.59 | 1.03 | 0.44 | 4.65 |
| HUGGIES ® Natural Care (Europe) | yes | yes | yes | 0.90 | 0.76 | 1.21 | 0.52 | 4.67 |
| TARGET ® UP & UP ® | no | no | yes | 0.41 | 0.61 | 0.68 | 0.60 | 4.41 |
| JOHNSON'S ® Baby Clean & Protect (Europe) | — | no | yes | — | — | — | 0.46 | 4.61 |
| JOHNSON'S ® Baby Extra Sensitive (Europe) | — | no | yes | — | — | — | 0.53 | 4.48 |

TABLE 5

| | SGI |
|---|---|
| Exemplary Wet Wipe of the Present Disclosure without an Emollient | 1.32 |
| Exemplary Wet Wipe of the Present Disclosure without an Emollient | 1.09 |
| Exemplary Wet Wipe of the Present | 1.07 |

TABLE 5-continued

| | SGI |
|---|---|
| Disclosure without an Emollient | |
| HUGGIES ® Simply Clean | 1.14 |
| HUGGIES ® One & Done Refreshing | 1.27 |
| HUGGIES ® Soft Skin | 1.28 |
| HUGGIES ® Soft Skin | 1.26 |

TABLE 5-continued

|  | SGI |
|---|---|
| HUGGIES ® Soft Skin | 1.32 |
| HUGGIES ® Soft Skin | 1.25 |
| HUGGIES ® Natural Care (UK) | 1.12 |
| HUGGIES ® Unistar (Italy) | 1.1 |
| HUGGIES ® Natural Care | 1.32 |
| PARENT'S CHOICE ™ Supreme Fragrance free | 1.04 |
| PARENT'S CHOICE ™ Supreme Fragrance free | 1.18 |
| PARENT'S CHOICE ™ Sensitive | 1.65 |
| PARENT'S CHOICE ™ Sensitive | 1.69 |
| PARENT'S CHOICE ™ Sensitive | 1.91 |
| TARGET ® UP & UP ®Unscented | 1.91 |
| TARGET ® UP & UP ®Sensitive | 1.81 |

TABLE 6

|  | Liquid Absorptive Capacity of Fibrous Substrate (g/g) |
|---|---|
| Exemplary Wipe of Present Disclosure | 13.6 |
| Exemplary Wipe of Present Disclosure | 14.8 |
| Exemplary Wipe of Present Disclosure | 16 |
| HUGGIES ® Natural Care | 11.5 |
| HUGGIES ® Natural Care | 9.78 |
| PAMPERS ® Baby Fresh | 12 |
| PAMPERS ® Baby Fresh | 7.32 |
| PAMPERS ® Thickcare | 7.52 |

Test Methods

Unless otherwise indicated, all tests described herein including those described under the Definitions section and the following test methods are conducted on samples that have been conditioned in a conditioned room at a temperature of 23° C.±2.2° C. and a relative humidity of 50%±10% for 24 hours prior to the test. All tests are conducted in such conditioned room.

For the dry test methods described herein (Liquid Absorptive Capacity, Basis Weight, Dry Drape), if the fibrous structure or wipe comprises a liquid composition such that the fibrous structure or wipe exhibits a moisture level of about 100% or greater by weight of the fibrous structure or wipe, then the following pre-conditioning procedure needs to be performed on the fibrous structure or wipe before testing. If the fibrous structure or wipe comprises a liquid composition such that the fibrous structure or wipe exhibits a moisture level of less than about 100% by weight but greater than about 10% by weight of the fibrous structure or wipe, dry the fibrous structure or wipe in an oven at 85° C. until the fibrous structure or wipe contains less than 3% moisture by weight of the fibrous structure or wipe prior to completing the dry test methods.

To pre-condition a fibrous structure or wipe comprising a moisture level of about 100% or greater by weight of the fibrous structure or wipe use the following procedure. Fully saturate the fibrous structure or wipe by immersing the fibrous structure or wipe sequentially in 2 L of fresh distilled water in each of 5 buckets, where the water is at a temperature of 23° C.±2.2° C. Gently, agitate the fibrous structure or wipe in the water by moving the fibrous structure or wipe from one side of each bucket to the other at least 5 times, but no more than 10 times for 20 seconds in each of the 5 buckets. Remove the fibrous structure or wipe and then place horizontally in an oven at 85° C. until the fibrous structure or wipe contains less than 3% moisture by weight of the fibrous structure or wipe. After the fibrous structure or wipe exhibits less than 3% moisture, remove from the oven and allow the fibrous structure or wipe to equilibrate to about 23° C.±2.2° C. and a relative humidity of 50%±10% for 24 hours prior to the testing. Care needs to be taken to ensure that the fibrous structure and/or wipe is not compressed.

For the wet test methods described herein (Tactile Sensory Coefficient of Friction, Cleaning Coefficient of Friction, Wet Drape, Saturation Gradient Index, Caliper, and Compressive Modulus), if the fibrous structure or wipe comprises a moisture level of 0% to less than about 100% by weight of the fibrous structure or wipe, then the following pre-conditioning procedure needs to be performed on the fibrous structure or wipe prior to testing. If the fibrous structure or wipe comprises a moisture level of about 100% or greater, then the following pre-conditioning procedure is not performed on the fibrous structure or wipe.

To pre-condition a fibrous structure or wipe comprising a moisture level of 0% to less than about 100% by weight of the fibrous structure or wipe, add an amount of distilled water to the fibrous structure or wipe to achieve a 3.5 g/g saturation loading on the fibrous structure or wipe.

After the fibrous structure or wipe is saturation loaded to a 3.5 g/g saturation loading, allow the fibrous structure or wipe to equilibrate to about 23° C.±2.2° C. and a relative humidity of 50%±10% for 24 hours prior to the testing. Care needs to be taken to ensure that the fibrous structure and/or wipe is not compressed.

Dry Test Methods

Liquid Absorptive Capacity Test Method

The following method, which is modeled after EDANA 10.4-02, is suitable to measure the Liquid Absorptive Capacity of any fibrous structure or wipe.

Prepare 5 samples of a pre-conditioned/conditioned fibrous structure or wipe for testing so that an average Liquid Absorptive Capacity of the 5 samples can be obtained.

Materials/Equipment

1. Flat stainless steel wire gauze sample holder with handle (commercially available from Humboldt Manufacturing Company) and flat stainless steel wire gauze (commercially available from McMaster-Carr) having a mesh size of 20 and having an overall size of at least 120 mm×120 mm
2. Dish of size suitable for submerging the sample holder, with sample attached, in a test liquid, described below, to a depth of approximately 20 mm
3. Binder Clips (commercially available from Staples) to hold the sample in place on the sample holder
4. Ring stand
5. Balance, which reads to four decimal places
6. Stopwatch
7. Test liquid: deionized water (resistivity>18 megaohms·cm)

Procedure

Prepare 5 samples of a fibrous structure or wipe for 5 separate Liquid Absorptive Capacity measurements. Individual test pieces are cut from the 5 samples to a size of approximately 100 mm×100 mm, and if an individual test piece weighs less than 1 gram, stack test pieces together to make sets that weigh at least 1 gram total. Fill the dish with a sufficient quantity of the test liquid described above, and allow it to equilibrate with room test conditions. Record the mass of the test piece(s) for the first measurement before fastening the test piece(s) to the wire gauze sample holder described above with the clips. While trying to avoid the creation of air bubbles, submerge the sample holder in the test liquid to a depth of approximately 20 mm and allow it to sit undisturbed for 60 seconds. After 60 seconds, remove both the sample and the sample holder from the test liquid. Remove all the binder clips but one, and attach the sample holder to the ring stand with the binder clip so that the sample may vertically hang freely and drain for a total of 120 seconds. After the conclusion of the draining period, gently remove the sample from the sample holder and record the sample's mass. Repeat for the remaining four test pieces or test piece sets.

Calculation of Liquid Absorptive Capacity

Liquid Absorptive Capacity is reported in units of grams of liquid composition per gram of the fibrous structure or wipe being tested. Liquid Absorptive Capacity is calculated as follows for each test that is conducted:

$$Liquid Absorptive\ Capacity = \frac{M_x - M_i}{M_i}$$

In this equation, $M_i$ is the mass in grams of the test piece(s) prior to starting the test, and $M_X$ is the mass in grams of the same test pieces(s) after conclusion of the test procedure. Liquid Absorptive Capacity is typically reported as the numerical average of at least five tests per sample.

Basis Weight Test Method

Basis weight is measured prior to the application of any end-use lotion, cleaning solution, or other liquid composition, etc. to the fibrous structure or wipe, and follows a modified EDANA 40.3-90 (February 1996) method as described herein below.

1. Cut at least three test pieces of the fibrous structure or wipe to specific known dimensions, preferably using a pre-cut metal die and die press. Each test piece typically has an area of at least 0.01 m².
2. Use a balance to determine the mass of each test piece in grams; calculate basis weight (mass per unit area), in grams per square meter (gsm), using equation (1).

$$Basis\ Weight = \frac{Mass\ of\ Test\ Piece\ (g)}{Area\ of\ Test\ Piece\ (m^2)} \quad (1)$$

3. For a fibrous structure or wipe sample, report the numerical average basis weight for all test pieces.
4. If only a limited amount of the fibrous structure or wipe is available, basis weight may be measured and reported as the basis weight of one test piece, the largest rectangle possible.

Wet Test Methods

Cleaning Coefficient of Friction

The Cleaning (kinetic) Coefficient of Friction (CoF) is measured using ASTM Method D 1894-01 with the following particulars. The test is performed on a constant rate of extension tensile tester with computer interface (a suitable instrument is the MTS Alliance using Testworks 4 Software, as available from MTS Systems Corp., Eden Prairie, Minn.) fitted with a coefficient of friction fixture and sled as described in D 1894-01 (a suitable fixture is the Coefficient of Friction Fixture and Sled available from Instron Corp., Canton, Mass.). The apparatus is configured as depicted in FIG. 1.c of ASTM 1894-01 using a stainless steel plane with a grind surface of 320 granulation as the target surface. A load cell is selected such that the measured forces are within 10-90% of the range of the cell. The tensile tester is programmed for a crosshead speed of 127 mm/min, and a total travel of 130 mm. Data is collected at a rate of 100 Hz. All testing is performed in a room where the temperature is controlled at 23° C.±2 C.°.

Wet wipes are collected from the top, middle, and bottom of the stack of wet wipes. As wipes are collected, ensure that the orientation of the wet wipes is maintained, i.e., cross direction CD versus machine direction MD, and surface of the wet wipe facing the top of package versus surface of the wet wipe facing the bottom of package. All wet wipes are maintained in a horizontal position and protected from evaporation (e.g., kept in zip lock bag) prior to testing.

Open the package of wet wipes and discard the top three (3) wet wipes from the stack. Collect the next six (6) wet wipes in the stack for testing. Invert the stack and discard the first three (3) wet wipes from the top of the stack. Collect the next six (6) wet wipes from the stack of wet wipes for testing. Separate the remaining stack of wet wipes into two approximately equal halves and collect three (3) wet wipes from the exposed interior of each. Divide the collected wet wipes into two groups, each group containing three (3) wet wipes from the top, middle, and bottom of the original stack of wet wipes. The first group of wet wipes is run with the surface facing the top of package facing the stainless steel plane, the second group of wet wipes is run with the surface facing the bottom of package facing the stainless steel plane.

Cut a test specimen 8.9 cm by 8.9 cm from the center of a wet wipe with its cut sides parallel and perpendicular to the machine direction of the substrate. Mount the specimen onto the foam rubber side of the sled by wrapping the edges around to the back of the sled and securing with adhesive tape. The specimen is oriented such that the specimen will be pulled along the machine direction MD of the specimen during the test.

Set up tensile test as described above. Zero the load cell and crosshead. Connect the sled to the lead line and place the sled, specimen surface down, onto the steel plane. The line should be secure under the pulley and taut, with less than 1.0 g force on the load cell. Start the test and collect force verses distance data. When the test is complete, remove the specimen from the sled. Clean the plane with isopropanol between each pull. From the resulting graph average the force in grams force (gf) between 20 mm and 128 mm. The kinetic coefficient of friction is calculated as the average force divided by the measured mass of the sled and reported to the nearest 0.01.

Repeat for each wet wipe in the two groups. Calculate the average of the kinetic coefficient of friction for each group (the first group with the surface of the wet wipe facing the top of package and the second group with the surface of the wet wipe facing the bottom of package) and record to the nearest 0.01. The Cleaning Coefficient of Friction is reported as the greater average of the two groups.

Tactile Sensory Coefficient of Friction

The Tactile Sensory Coefficient of Friction measurement is performed on a Freeslate Core Module 3 Robot (available from Freeslate, Sunnyvale, Calif.) using a Buna-N ball tipped probe that records the force in both the Y and Z direction as it is moved across the wipe's surface. All testing is performed in a room where the temperature is controlled at 23° C.±2 C.°.

The CM3 robot is configured in a Track, Friction, Wear sequence with the following standard modules:

Plate Gripper Arm;
Tribology (Friction) Arm;
Barcode station with deck-mounted barcode reader;

Right shoulder loading deck;

Three-position vacuum chuck deck element; and

Racks for holding the samples and disposable spherical probe tips

The Friction arm is configured with two 1 Kg Load cells (available as Model LSP-1 from Transducer Techniques, Temecula, Calif.) mounted to acquire force data in the Y and Z directions. The arm is equipped with a vacuum chuck for a ⅜" spherical probe. The chuck is loaded with two conical springs (P/N V15346 from Freeslate). The system is controlled and integrated using Freeslate LEA software suite (Library Studio, Automation Studio, Polyview).

Specimens are mounted on magnetic steel plates 4.68"L×3"W×0.140" thick and held in place using magnets. A disposable friction tip is made of Buna-N with a diameter of ⅜ in ±0.003 in (0.003 in sphericity) having a Shore A hardness of 70 (P/N ASIN: B000FMWGUA available from AmazonSuppy, Seattle, Wash.).

Wet wipes are collected from the top, middle, and bottom of the stack of wet wipes. As wet wipes are collected ensure that the orientation is maintained, i.e., cross direction CD versus machine direction MD, and surface of the wet wipe facing the top of package versus surface of the wet wipe facing the bottom of package. All wet wipes are maintained in a horizontal position and protected from evaporation (e.g. kept in a zip lock bag) prior to testing.

Open the package of wet wipes and discard the top three (3) wet wipes from the stack. Collect the next four (4) wet wipes from the stack for testing. Invert the stack of wet wipes and discard the first three (3) wet wipes from the top of the stack. Collect the next four (4) wipes for testing. Separate the remaining stack of wet wipes into two approximately equal halves and collect two (2) wet wipes from the exposed interior of each. Separate the collected wet wipes into two substantially similar groups, with each group containing two (2) wet wipes from the top, middle, and bottom of the original stack of wet wipes. The first group is analyzed with the surface of the wet wipe facing the top of package facing upward (toward the probe) and the second group is analyzed with the surface of the wet wipe facing the bottom of package facing upward.

Cut a test specimen 12 cm in the machine direction MD by 7.6 cm in the cross direction CD from the center of a wet wipe with its cut sides parallel and perpendicular to the machine direction MD of the wet wipe. Place the specimen flat onto a sample plate with the specified surface facing upward and the machine direction MD direction parallel to the long side of the plate. Attach the specimen via magnets to hold firmly to the plate. Specimens are prepared one at a time and loaded manually onto the robot. Place the loaded sample plate and rack onto the right shoulder loading position. The robot is programmed to perform the following steps.

The rack and sample is moved to the barcoding station by the plate gripper arm, where a unique barcode is applied. The rack and sample is moved via the plate gripper arm to the vacuum chuck station and locked into position via a vacuum source. The friction arm is moved to pick up a ball. The ball is moved over to the specimen and is positioned approximately 5 mm over its surface near the corner of the specimen. The site is selected such that no emboss or clump is located underneath the probe. The probe is lowered until a 0.625N normal force is measured against the surface and the probe height (Z-position) is recorded. The probe is then raised back to 5 mm above the surface, and moved to the test site for the first measurement stroke.

The probe is lowered to contact the surface at the pre-calibrated Z-position. After 2 seconds the stroke is started and is advanced at 5 mm/s for a stroke length of 50 mm in the machine direction MD of the specimen. Data for normal force (N), lateral force (N) and distance (mm) are collected at a rate of 100 Hz. The ball is discarded and a new ball picked up between each stroke. The new ball is positioned 3.8 mm to the right of the previous stroke and another stroke is performed parallel to the first. Strokes are repeated in like fashion for a total of 5 strokes per specimen. All collected wet wipes are sequentially prepared and analyzed as described.

The kinetic coefficient of friction is calculated based on the force data acquired between 15 mm and 35 mm of the stroke. The lateral force is averaged and the normal force is averaged for each stroke and recorded to the nearest 0.01 N. The kinetic coefficient of friction is calculated as Lateral Force divided by Normal Force and recorded to the nearest 0.01. Calculate the average kinetic coefficient of friction for each group (the first group with the surface of the wet wipe facing the top of package and the second group with the surface of the wet wipe facing the bottom of package) and record to the nearest 0.01. The Tactile Sensory Coefficient of Friction is reported as the lower average of the two groups.

Drape Ratio

The Drape Ratio is calculated by measuring the circular bend of the wet wipes in both the wet and dry state and calculating the wet to dry ratio. The circular bend is measured using ASTM D 4032 with the following particulars. The test is performed on a constant rate of extension tensile tester with computer interface (a suitable instrument is the MTS Alliance RT/1 using Testworks 4 Software, as available from MTS Systems Corp., Eden Prairie, Minn.) fitted with a platform and plunger as described in ASTM 4032. The piston position is set to 3 mm above the top surface of the platform. The crosshead screw motor is set to its maximum acceleration. Program the tensile tester for a compression test. The crosshead is set to descend at 990 mm/min for 60 mm. Data is collected at 100 Hz. All testing is performed in a room where the temperature is controlled at 23° C.±2 C.°.

Wet wipes are collected from the top, middle, and bottom of a stack of wet wipes. As wet wipes are collected ensure that the orientation is maintained, i.e., cross direction CD versus machine direction MD, and surface of the wet wipe facing the top of package versus surface of the wet wipe facing the bottom of package. All wet wipes are maintained in a horizontal position and protected from evaporation (e.g., kept in a zip lock bag) prior to testing.

Open the package of wet wipes and discard the top three (3) wet wipes from the stack. Collect the next eight (8) wet wipes from the stack for testing. Invert the stack of wet wipes and discard the first three (3) wipes from the top of the stack. Collect the next eight (8) wet wipes for testing. Separate the remaining stack of wet wipes into two approximately equal halves and collect four (4) wet wipes from the exposed interior of each. Divide the collected wet wipes into four substantially similar groups (A through D), each group containing two (2) wet wipes from the top, middle, and bottom of the original stack of wet wipes. Run groups A and B immediately with the wet wipes in their wet state as specified below. Individually lay each wet wipe from groups C and D flat on horizontal racks to dry overnight.

Cut a test specimen 7.6 cm by 7.6 cm from the center of a wet wipe with its cut sides parallel and perpendicular to the machine direction MD of the wet wipe. Repeat for all wet wipes in Groups A and B.

Set up the tensile tester as described above. Zero the crosshead and load cell. Place a specimen from group A, with the surface facing the top of package facing upward on the platform and centered under the plunger. Start the test and collect force versus distance data. From the resulting curve, record the maximum peak force. Repeat testing for the remaining wet wipes of Group A. Group B is tested in like fashion, except that the specimen is placed on the platform with the surface facing the bottom of package facing upward. Average the maximum peak force values (N=12) for Group A and B, and report as Wet Circular Bend to the nearest 0.01 N.

After drying for 12 hours, prepare wet wipes in groups C and D. Cut a test specimen 10.2 cm by 10.2 cm from the center of a wet wipe with its cut sides parallel and perpendicular to the machine direction MD of the wet wipe. Repeat for all wet wipes in Groups C and D. In like fashion to groups A and B, analyze group C (the surface of the wet wipes facing the top of package facing upward) and D (the surface of the wet wipes facing the bottom of package facing upward) calculating the maximum peak force for each specimen. Average the maximum peak force values (N=12) for Group C and D, and report as Dry Circular Bend to the nearest 0.01 N.

Calculate the Drape Ratio as the Wet Circular Bend value divided by the Dry Circular Bend value and report to the nearest 0.01.

Caliper

Caliper of the wet wipe is measured as specified in EDANA 30.5. Wet wipes are sampled from the top, middle, and bottom of a package of wet wipes. All testing is performed in a room where the temperature is controlled at 23° C.±2 C.°.

Open the package of wet wipes and discard the top three (3) wet wipes from the stack. Collect the next two (2) wet wipes for testing. Invert the stack of wet wipes and discard the first three (3) wet wipes from the top of the stack. Collect the next two (2) wet wipes for testing. Separate the remaining stack of wet wipes into two approximately equal halves and collect one (1) wipe from the exposed interior of each. All wet wipes are maintained in a horizontal position and protected from evaporation (e.g., kept in a zip lock bag) prior to testing. Measure the caliper of a wet wipe near each corner of the wet wipe and at the center of the wet wipe (a total of 5 measures per wet wipe) and record to the nearest 0.01 mm. Repeat for all six collected wet wipes. Average all thickness values and report as Caliper to the nearest 0.01 mm.

Compression

Compression reported as compressibility, Near Zero Load (NZL) Caliper and Compressive Modulus is measured on a constant rate of extension tensile tester with computer interface (a suitable instrument is the MTS Alliance using Testworks 4 Software, as available from MTS Systems Corp., Eden Prairie, Minn.) fitted with a bottom circular platen 10 cm in diameter, a top circular platen with an area of 1.00 in$^2$, and a 25 N load cell. The platens are adjusted to be orthogonal to the pull axis of the tensile tester and parallel to each other. An initial gage length of 5.00 mm is set between the two platens. Program the tensile tester for a compression test. Lower the top platen down at a rate of 5 mm/min until a force of 310 g is measured at the load cell. Data is collected at a rate of 100 Hz. All testing is performed in a room where the temperature is controlled at 23° C.±2 C.°.

Wet wipes are sampled from the top, middle, and bottom of a package of wet wipes. Open the package of wet wipes and discard the top three (3) wipes from the stack of wet wipes. Collect the next two (2) wipes for testing. Invert the stack and discard the first three (3) wet wipes from the top of the stack. Collect the next two (2) wet wipes for testing. Separate the remaining stack of wet wipes into two approximately equal halves and collect one (1) wet wipe from the exposed interior of each. All wet wipes are maintained in a horizontal position and protected from evaporation (e.g., kept in a zip lock bag) prior to testing.

Measure the compression of a wet wipe at five sites, once near each corner of the wet wipe and then at the center of the wet wipe (a total of 5 measures per wipe). Set the gage length. Zero the load cell and crosshead position. Place a wet wipe on the bottom platen with the site to be measured centered underneath the upper platen. Start the test and collecting the force versus distance data. Repeat for all five sites on the wet wipe. Analyze the remaining collected wet wipes in like fashion.

For each measure construct a distance (mm) versus log of pressure (log(grams/inch$^2$)) (log(g/in$^2$)) curve for the data points between 10 g and 300 g. Calculate the values below for each analysis.

Compressibility (mm/log(gsi))=slope

Near-Zero caliper (mm)=y-intercept

Compressive Modulus (log(gsi))=y-intercept/(negative of the slope)

Average the above results for all wet wipes and report each to the nearest 0.01 units.

Peak Complex Viscosity Test Method

This method is suitable for determination of peak complex viscosity of a liquid composition. A Haake Rheostress 600 rotational rheometer available from Thermo Fisher Scientific of Waltham, Mass. or equivalent instrument is used. A 60 mm diameter parallel plate fixture is used and the temperature of the specimen is controlled to 25±1° C. during the viscosity measurement by means of a suitable circulating water bath.

The instrument is programmed to run in Amplitude Sweep mode at a frequency of 0.16 Hz starting at a shear stress Tau=0.05 Pa and ending at Tau=25.6 Pa with a maximum measurement time of 300 seconds. The amplitude is increased in 10 steps on a linear scale using the following Tau values:

| Step | Tau [Pa] |
| --- | --- |
| 1 | 0.05 |
| 2 | 0.10 |
| 3 | 0.20 |
| 4 | 0.40 |
| 5 | 0.80 |
| 6 | 1.60 |
| 7 | 3.20 |
| 8 | 6.40 |
| 9 | 12.80 |
| 10 | 25.60 |

The instrument is calibrated for inertia and zero gap according to the procedures specified by the instrument manufacturer. The plates are separated and cleaned with a suitable solvent and allowed to dry. A sufficient quantity of the liquid composition is deposited onto the center of the base plate using a suitable pipette or equivalent to ensure that the liquid composition will completely fill the gap when the plates are brought together. Typically this is approximately 2.5 ml of the lotion composition. The gap is then closed to 0.800 mm and the sample is trimmed by running a rubber policeman or equivalent around the periphery of the plates to remove any excess liquid. The test is then initiated and the relevant data (complex viscosity Eta* as a function of shear stress Tau) are acquired.

The Peak Complex Viscosity is the highest recorded value for Eta*. This value can be obtained directly from the raw data.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wet wipe comprising:
   a fibrous structure, wherein the fibrous structure comprises filaments and solid additives; and
   a liquid composition comprising a plurality of droplets suspended in water, each droplet comprising a liquid core surrounded by a solid film, each liquid core comprising a lipophilic emollient, and each solid film comprising a plurality of clay mineral particles each having a particle size of about 1 micron;
   wherein the wet wipe exhibits a Tactile Sensory Coefficient of Friction of less than 0.60 as measured according to a Tactile Sensory Coefficient of Friction Test Method;
   wherein the fibrous structure is layered;
   wherein the fibrous structure has a basis weight of from about 40 g/m² to about 60 g/m²;
   wherein the fibrous structure has a density of less than 0.10 g/cm³;
   wherein the liquid composition is present at from about 200% to about 400% of the basis weight of the fibrous structure;
   wherein the filaments and the solid additives are present in the fibrous structure at a first weight ratio of at least 1:7; and
   wherein the wet wipe has a Cleaning Coefficient of Friction of greater than 0.50 as measured according to a Cleaning Coefficient of Friction Test Method.

2. The wet wipe according to claim 1, wherein at least one of the solid additives comprises a fiber comprising a wood pulp fiber, wherein the wood pulp fiber is selected from: treated or untreated softwood fibers, Southern Softwood Kraft pulp fibers, Northern Softwood Kraft pulp fibers, treated or untreated hardwood fibers, *Eucalyptus* pulp fibers, *Acacia* pulp fibers, and combinations thereof; and wherein the filaments comprise at least one of a natural polymer or a thermoplastic polymer, wherein the natural polymer is selected from: starch, starch derivatives, cellulose, cellulose derivatives, hemicelluloses, hemicelluloses derivatives and mixtures thereof; and wherein the thermoplastic polymer is selected from a group consisting of: polypropylene, polyethylene, polyester, polylactic acid, polyhydroxyalkanoate, polyvinyl alcohol, polycaprolactone and mixtures thereof; and wherein at least one surface of the fibrous structure comprises a layer of filaments.

3. The wet wipe according to claim 1, wherein the liquid composition comprises at least one from a group consisting of: a rheology modifier, an emulsifier, and a preservative.

4. The wet wipe according to claim 1, wherein the fibrous structure has a Liquid Absorptive Capacity of greater than 12 g/g as measured according to a Liquid Absorptive Capacity Test Method.

5. The wet wipe according to claim 1, wherein the wet wipe has a Wet to Dry Drape Ratio of less than about 0.80 measured according to a Wet to Dry Drape Ratio Test Method.

6. The wet wipe according to claim 1, wherein the wet wipe exhibits a Compressive Modulus of greater than about 4.75 [log(gsi)] measured according to a Compressive Modulus Test Method.

7. A wet wipe comprising:
   a fibrous structure, wherein the fibrous structure comprises filaments and solid additives; wherein at least one of the filaments comprises a thermoplastic polymer or a natural polymer; and wherein the solid additives comprise a fiber; and wherein at least one surface of the fibrous structure comprises a layer of filaments; and
   a liquid composition comprising a plurality of droplets suspended in greater than 90% water, each droplet comprising a liquid core surrounded by a solid film, each liquid core comprising a lipophilic emollient, and each solid film comprising a plurality of clay mineral particles each having a particle size of about 1 micron;
   wherein the wet wipe exhibits a Wet to Dry Drape Ratio of less than about 0.80 as measured according to a Wet to Dry Drape Ratio Test Method;
   wherein the fibrous structure is layered;
   wherein the fibrous structure has a basis weight of from about 40 g/m² to about 60 g/m²;
   wherein the fibrous structure has a density of less than 0.10 g/cm³;
   wherein the liquid composition is present at from about 200% to about 400% of the basis weight of the fibrous structure;
   wherein the filaments and the solid additives are present in the fibrous structure at a first weight ratio of at least 1:7; and
   wherein the wet wipe has a Cleaning Coefficient of Friction of greater than 0.50 as measured according to a Cleaning Coefficient of Friction Test Method.

8. The wet wipe according to claim 7, wherein the liquid composition comprises at least one from a group consisting of: a rheology modifier, an emulsifier, and a preservative.

9. The wet wipe according to claim 7, wherein the fibrous structure has a Liquid Absorptive Capacity of greater than 12 g/g as measured according to a Liquid Absorptive Capacity Test Method.

10. The wet wipe according to claim 7, wherein the wet wipe has a Tactile Sensory Coefficient of Friction of less than 0.60 measured according to a Tactile Sensory Coefficient of Friction Test Method.

11. The wet wipe according to claim 7, wherein the wet wipe exhibits a Compressive Modulus of greater than about 4.75 [log(gsi)] measured according to a Compressive Modulus Test Method.

12. The wet wipe according to claim 1, wherein a second weight ratio of the emollient and the clay mineral is in a range of about 1:30 to about 30:1.

13. The wet wipe according to claim 7, wherein a second weight ratio of the emollient and the clay mineral is in a range of about 1:30 to about 30:1.

* * * * *